（12） United States Patent
Akay et al.

(10) Patent No.: US 8,898,955 B2
(45) Date of Patent: Dec. 2, 2014

(54) SYNTHETIC SYMBIOTIC SYSTEM AS SOIL ADDITIVES TO DELIVER ACTIVE INGREDIENTS THROUGH PLANT ROOTS FOR ENHANCED PLANT AND CROP YIELD

(75) Inventors: Galip Akay, Newcastle Upon Tyne (GB); David Robert Burke, Newcastle Upon Tyne (GB); Teresa Manguangua Ndlovu, Newcastle upon Tyne (GB)

(73) Assignee: University of Newcastle Upon Tyne, Newcastle Upon Tyne (GB)

( * ) Notice: Subject to any disclaimer, the term of this patent is extended or adjusted under 35 U.S.C. 154(b) by 883 days.

(21) Appl. No.: 13/123,060

(22) PCT Filed: Oct. 6, 2009

(86) PCT No.: PCT/GB2009/002380
§ 371 (c)(1),
(2), (4) Date: Sep. 2, 2011

(87) PCT Pub. No.: WO2010/040996
PCT Pub. Date: Apr. 15, 2010

(65) Prior Publication Data
US 2011/0308154 A1 Dec. 22, 2011

(30) Foreign Application Priority Data

Oct. 7, 2008 (GB) .................................. 0818284.2

(51) Int. Cl.
A01G 31/00 (2006.01)
A01H 3/00 (2006.01)
(52) U.S. Cl.
CPC ........................................ A01H 3/00 (2013.01)
USPC ........................................................ 47/59 S

(58) Field of Classification Search
USPC ................................ 47/59 S, 58.1 SC, 1.01 R
See application file for complete search history.

(56) References Cited

U.S. PATENT DOCUMENTS 5,071,747 A * 12/1991 Hough et al. ................... 435/41

FOREIGN PATENT DOCUMENTS

GB WO0034454 * 6/2000

* cited by examiner

Primary Examiner — Monica Williams
(74) Attorney, Agent, or Firm — Galgano & Associates, PLLC; Thomas M. Galgano; Jessica G. Bower

(57) ABSTRACT

A plant growth support medium is described to enhance soil characteristics and provide where required, improved water, or nutrient contents. In addition the medium can be inoculated with microorganisms to aid soil characteristics and provide interactions within micron-scale environment between plant roots, water, nutrients and where applicable, bacteria and root exudates. This micro-environment provides direct delivery of active ingredients to the plant roots. The medium comprises a polymeric material having a primary pore size of greater than 30 micron. The walls of the pores are elastic, enabling the pore to swell in size to retain water, solutes or other biologically useful components and allow root penetration through them. Sulphonation of the walls renders the walls more hydrophilic so attracting water into the pores and also increasing the wall elasticity. Capillaries can be provided to interconnect pores and allow root penetration into the medium. The pore walls can be granular in character to allow water, nutrient and where applicable, bacterial metabolites and messenger molecules passage between adjacent pores and plant roots.

16 Claims, 38 Drawing Sheets

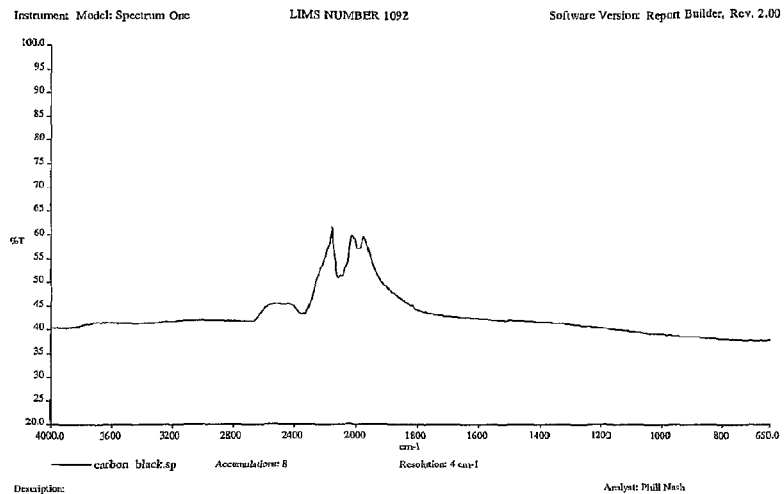
Figure 1(b)
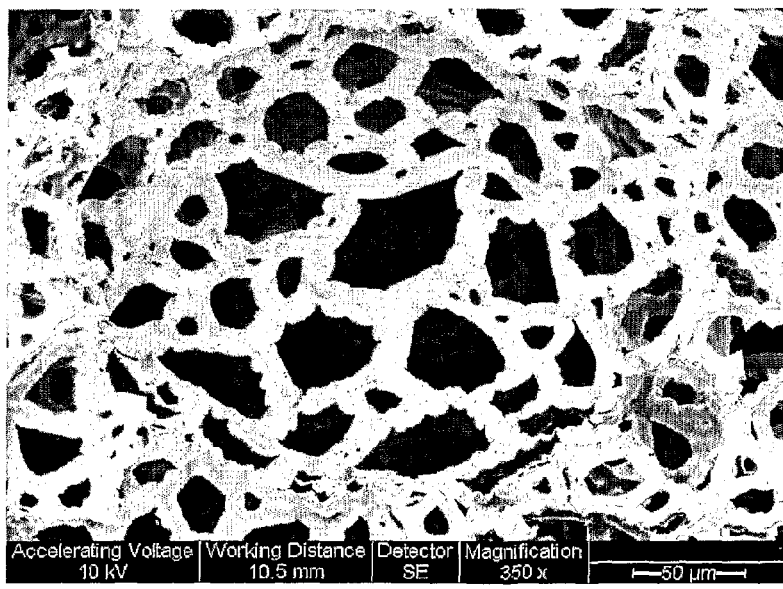
Figure 2(a) Acid form of sulphonated polymer with phase volume of 90%. Dosing time 5 minute at 300rpm, extra mixing time is 1 minute at 150 rpm. General structure showing a large coalescence pore (ca. 250 micron) surrounded by smaller primary pores (ca. 70 micron). Magnification=350

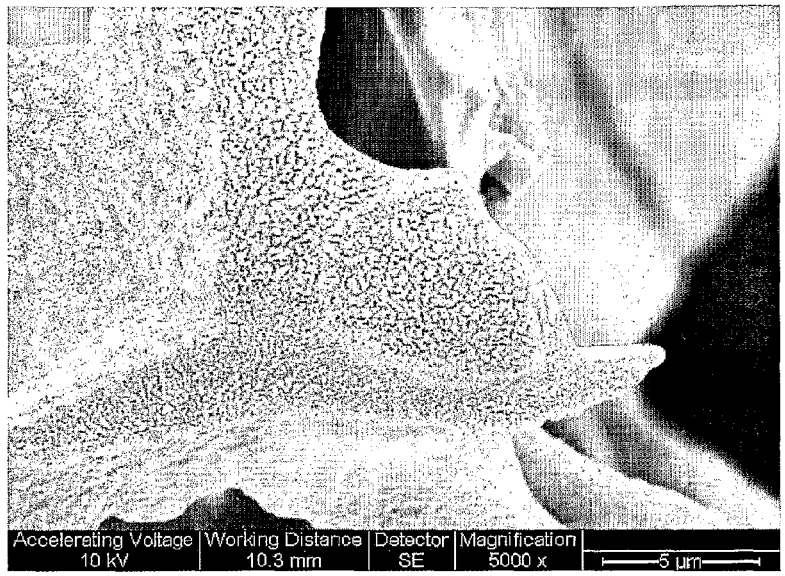
Figure 2 (b). Same as Fig. 2(a) showing the detail of wall surface and wall inner structure Magnification= 5k
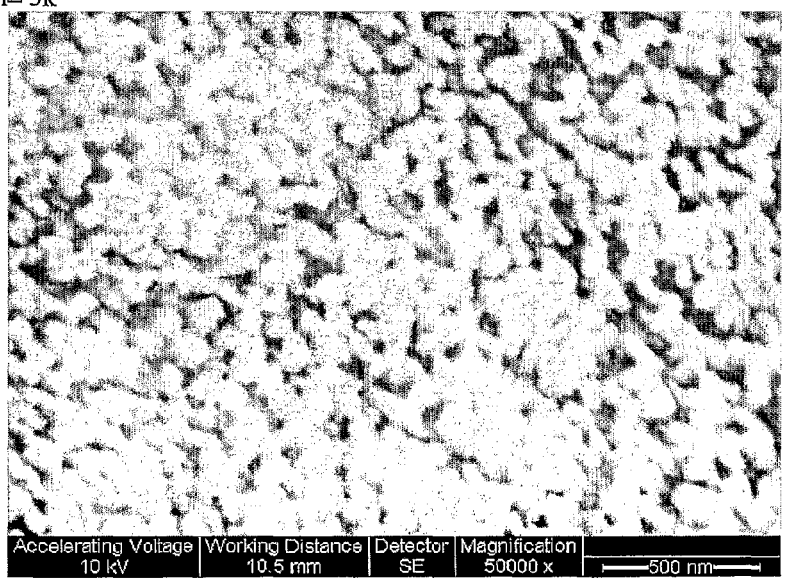
Figure2(c). Same as in Figure 2(a) showing the nano-porosity of the wall surface at Magnification= 50k

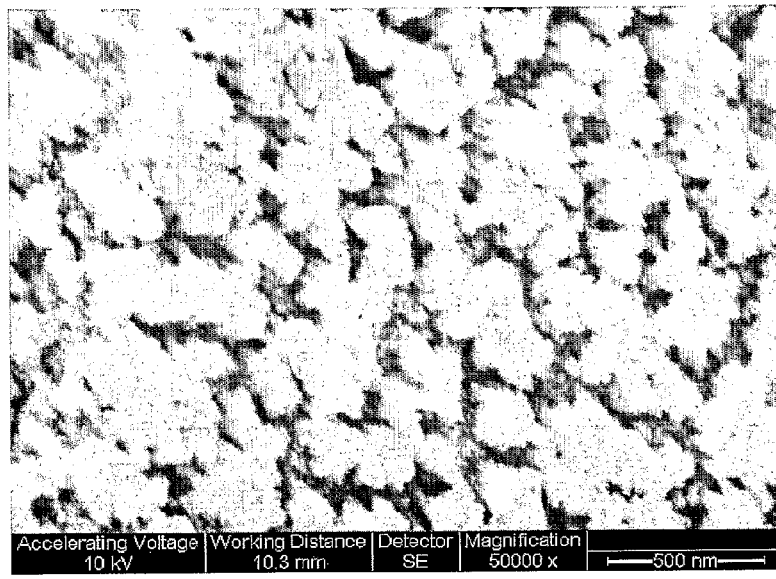
Figure 2 (d). Same as Figure 2(a) showing the nano-structure of the wall interior at Magnification= 50k.
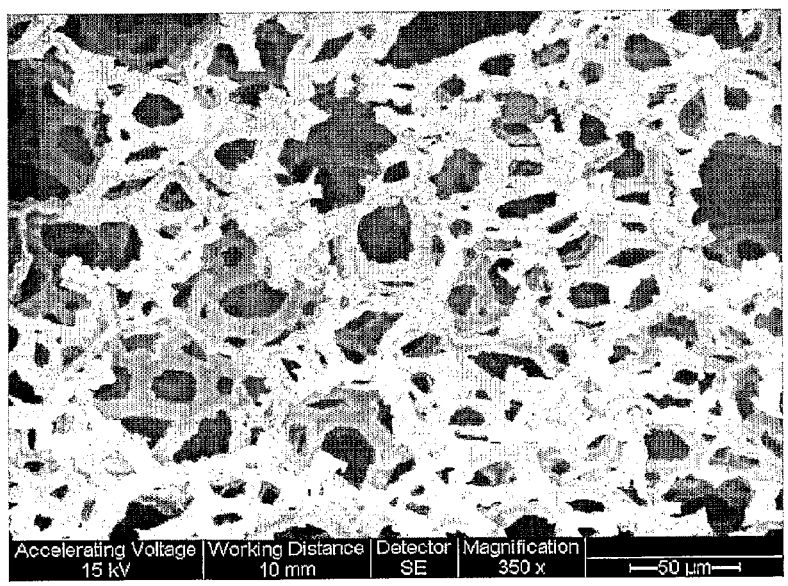
Figure 2(e). Sulphonated PolyHIPE Polymer (same as in Figure 2a) after neutralization with ammonium hydroxide showing a number of primary pores (ca. 70 micron) at Magnification= 350.

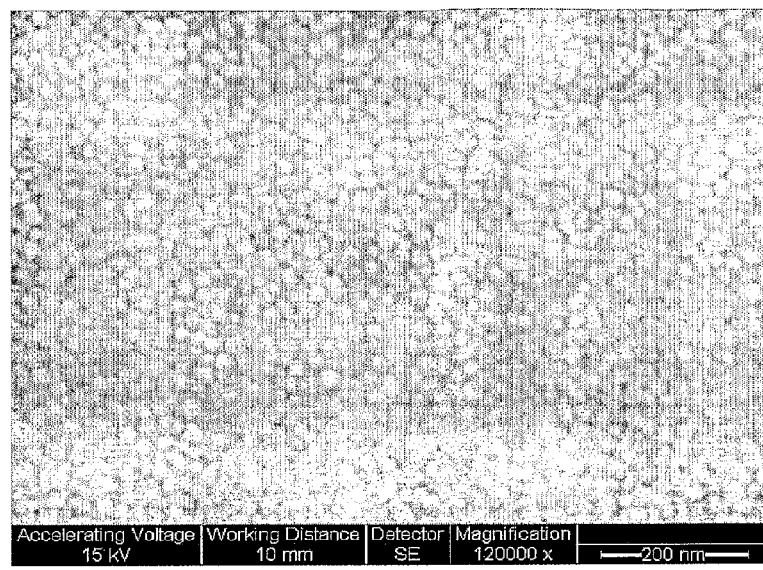
Figure 2(f). Same as in Figure 2(e), showing the nano-porosity of the surface. Note that the nano-structure is finer and porosity is reduced compared with the acid form. Magnification= 120k, Left: (C1) Control with normal watering, Right: (P1) PolyHIPE treatment with normal watering
Normal watering = 200ml water twice per week Left: (C2) Control with reduced watering, Right: (P2) PolyHIPE treatment with reduced watering
Reduced watering = 100ml water twice per week Left - Right: (C1) Control with normal watering, (P1)PolyHIPE treatment with normal watering, (C2) Control with reduced watering, (P2) PolyHIPE treatment with reduced watering

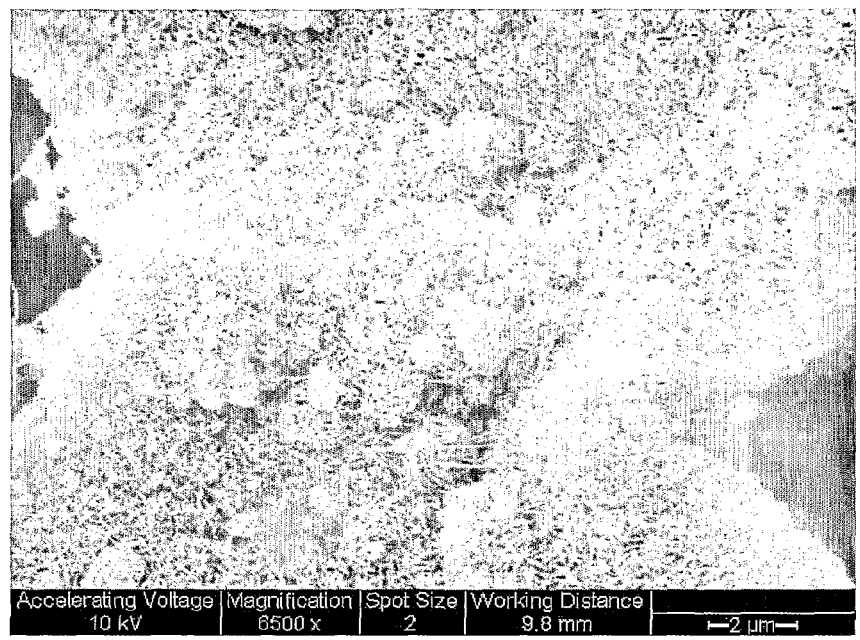
Figure 20 (c)
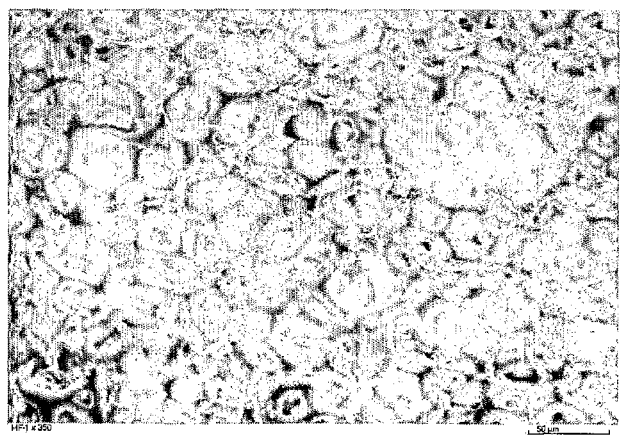
Figure 21(a).: Mycorrhizal fungi on PHP pore walls at low magnification

Figure 21(b): Mycorrhizal fungi on PHP pore walls at high magnification
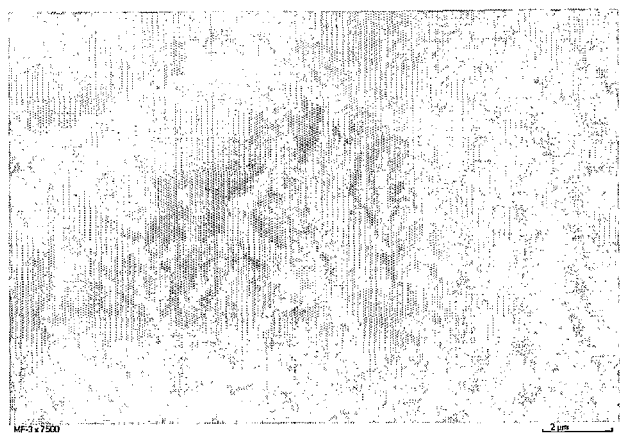
Figure 21(c): Mycorrhizal fungi on PHP pore walls at higher magnification

SYNTHETIC SYMBIOTIC SYSTEM AS SOIL ADDITIVES TO DELIVER ACTIVE INGREDIENTS THROUGH PLANT ROOTS FOR ENHANCED PLANT AND CROP YIELD

This invention describes a process for the preparation of nano-structured macro-porous hydrophilic cross-linked ionic polymer particle systems with or without biological activity used as soil additives which allow the penetration of plant roots into and through the particles whereby growth rate and yield of biomass and crop are enhanced, especially under water and fertilizer stress. When applied to growth from seeds or seedlings, the process also provides favorable conditions for growth by providing nutrients to the growing plant in order to establish itself.

When such plants are transplanted, the favorable growth conditions are still maintained thus enabling a plant to establish itself in the more hostile new environment. The enhancement of plant growth and crop enhancement is referred to as Agro-Process Intensification (A-PI) and the synthetic media for the promotion of interactions between plat roots, water, nutrients and where applicable, microorganisms (such as bacteria and/or fungi) for A-PI is referred to as a Synthetic Symbiotic System, (SSS). The SSS material (polymer) is essentially a nano-structured micro-porous (NSMP) elastic/spongy ionic, cross-linked, hydrophilic polymer with or without biologically active species such as bacteria and fungi and which allows the interactions between the plant roots, water, nutrients and bacteria on a micron scale.

The beneficial effects of the SSS are summarised below:
1. the dispersion of highly water adsorbing (hydrophilic) and swelling nano-structured micro-porous cross-linked ionic polymer particles in soil results in more efficient water management which results in biomass and crop enhancement. Unlike other water adsorbing soil conditioners, SSS polymer remains in the soil and is not easily washed away or chemically or biologically degraded.
2. Storing fertilizers within the pores of the particulate SSS polymer results in direct-targeted slow and nutrient release to the plant roots.
3. If the plant roots penetrate into the SSS polymer, the plant benefits from the presence of nutrients and water already adsorbed by the polymer which can at the same time act as an ion exchange medium because of the presence of ionic moieties.
4. Inoculation and colonization of the particulate SSS polymer with nitrogen fixing bacteria result in bacterial infection of the roots and enable the symbiotic nitrogen transfer from air to legumes resulting in enhanced crop nitrogen, phosphorus as well as metal concentration.
5. Mixed microorganisms (such as *rhizobium* and beneficial soil fungi, mycorrhizal) inoculation results in the transfer of nitrogen to non-legume plants and efficient transfer of nutrients, such as phosphorous, to the plant.
6. Inter-cropping of legumes with non-legumes in the presence of inoculated SSS-polymer also results in common root association with SSS-polymer and nitrogen sharing between the plants.
7. By growing plant seed on a SSS-polymer in a pot and subsequently transplanting, the chance of survival increases and of establishing the plant in a new environment.

Based on greenhouse experiments on model plants, grass and jatropha (which can not fix nitrogen) and pea and soybean (which can fix nitrogen), the benefits of the SSS are summarized below:

1. elastic/spongy SSS polymer allows soil micro-organisms, bacterial or fungi, in-growth
2. Enhanced metal concentration in crops.
3. Large enhancement under arid conditions.
4. Enhancement as the number of harvests increase as fertilizer is washed away.
5. Infection of legumes enhanced when root system goes through the biologically active SSS-polymer media.
6. Root morphology is modified when roots grow through SSS-polymer media.
7. Mixed bacterium inoculation of SSS-polymer can result symbiotic enhancement since bacteria and root are within a few tens of microns of each other.

DESCRIPTION OF PRIOR ART

AgroProcess Intensification (A-PI) is important under stress conditions which would be enhanced in the event of global warming occurring. In this case, water and nitrogen stress in agriculture would increase while the increased demand for biomass, food and fertilizers would make any biomass based energy/chemicals feedstock technologies unsustainable. The present invention discloses how plant growth through targeted water regulation, fertilizer release and biological nitrogen fixation can be achieved simultaneously. Here, targeting of water, biological nitrogen fixation and delivery of fertilizer (including nitrogen) is achieved by associating plant roots with SSS-polymer. This invention differs fundamentally from other biomass/crop enhancement techniques using soil conditioners or slow release fertilizers or inter-cropping because, in the present invention, the SSS-polymer is associated with the plant roots thus the delivery of the nutrients, water and the infection of roots (leading to nodule formation for biological nitrogen fixation) is direct and concentrated at the root hairs. The summary below outlines the technology available for plant and crop enhancement.

Super-absorbent Polymers (SAPs)

There is great potential for the use of polymers in agricultural and horticultural applications where there are soils of low water holding capacity and in semi-arid regions. In many semi-arid countries, irrigation of crops is carried out using low quality water therefore exacerbating soil salinity. Super-absorbent polymers and hydrogels have been reported to absorb up to 2400 times their weight in deionized water even under pressure. The application of hydrogels has been shown to supply water to growing crops, reduce the impact of water deficit stress and to reduce irrigation requirement, lower the death rate of plants, improve fertiliser retention in soils and increase plant growth (Mohana Raju, K., Padmanabha Raju, M. and Murali Mohan, Y. (2003). *Synthesis of Superabsorbent Copolymers as Water Manageable Materials*. Polymer Int. 52: 768-772). Plant growth benefits in terms of plant height, leaf width, total dry weight, and increased length of time before the plant begins to wilt have been observed. This is achieved via the influence of the polymer or hydrogel on a range of Characteristics, e.g. soil permeability, density, structure, texture, compaction, aeration, erosion, and microbial activity, as well as affecting water run-off, evaporation and infiltration rates (Abd El-Rehim, H. A., H., E.-S. A. and Abd El-Mohdy, H. L. (2004). *Radiation Synthesis of Hydrogels to Enhance Sandy Soils Water Retention and Increase Plant Performance*. J Appl Polymer Sci Vol. 93: 1360-1371). However, due to poor cross-linking, hydrogels are prone to being readily degraded and washed away.

Slow Release Fertilisers

Fertiliser application is used to produce high yields and quality of agricultural crops. Excess application and poor use efficiency often leads to leaching and run-off, which results in eutrophication of water systems due to 'algal blooms' in lakes and 'red tides' in estuaries. It is estimated that around 50-70% of the applied fertilizer can be lost to the environment. To help increase the efficiency of fertiliser use, slow- and controlled-release systems have been developed to release the fertiliser to the plants at a rate at which it can be utilised, therefore minimising loss to the environment through leaching and run-off.

Microbial Inoculation

Inoculation is simply the process of applying live plant-beneficial microorganisms (bacteria and fungi) in a carrier material which can be either organic, inorganic, natural or synthesized. The desired effects of inoculants on plant growth include nitrogen fixation in legumes, biocontrol of soil-borne diseases, the enhancement of mineral uptake, weathering of soil minerals and nutritional or hormonal effects. Inoculation of soil with rhizobacteria results in the infection of roots of compatible plants to form effective nodules. Beneficial fungi such as mycorrhizas also form symbiotic association with plant through roots and help phosphate uptake. A variety of methods can be used to inoculate crops, with the most common being to coat the seed with a powdered inoculant which can then infect the seed as it begins to germinate. Depending on the soil type, host plant and bacteria, the dispersion of rhizobacteria from the point of inoculation towards the roots will depend on either the active motility of the bacteria and the passive movement of bacteria in water or on vectors. However, studies examining pea root colonisation by *Pseudomonas fluorescens* and also potato root colonisation by *Pseudomonas* species strains indicate that irrigation and water flow is the most effective method for transporting bacteria to the roots. In the shortage of water, transport of bacteria will be limited.

A number of *Rhizobium* strains can stimulate plant growth without nodule formation, via promoting nutrition, accelerating mineralisation processes, or by protecting against harmful soil micro-organisms. However, the yield response in such cases is obviously less than where nitrogen is fixed. Pea (*Pisum sativum*) crops are an important source of protein in human diets, as well as providing forage for animal feed. Peas are nodulated by *Rhizobium leguminosarum* biovar viciae (Rlv) which is commonly found in European arable soils. All Rhizobia show host specificity to some extent, and Rlv is capable of modulating all species in the tribe Vicieae, which includes the genera *Vicia, Lathyrus, Pisum* and *Lens*. Usually in legume-*Rhizobium* symbiosis it is host specificity that determines the attachment of *Rhizobium* and *Bradyrhizobium* species to the legume roots, but studies show that for the *Rhizobium*-pea system, it is the conditions under which the rhizobia are grown that strongly influences the attachment to roots (Abd El-Rehim, H. A., H., E.-S. A. and Abd El-Mohdy, H. L. (2004). *Radiation Synthesis of Hydrogels to Enhance Sandy Soils Water Retention and Increase Plant Performance*. J Appl Polymer Sci Vol. 93: 1360-1371). This is believed to be due to low inoculation efficiency of the Rlv strains and poorly studied strain-cultivar specificity.

The attachment of *Rhizobium leguminosarum* to pea root hairs is known to be dependant on the incubation pH and growth phase, with the optimal attachment being at pH 7.5 and with bacteria in the early stationary phase of growth. The amount of nitrogen that is fixed via the *Rhizobium* and pea (*Pisum sativum* L.) symbiosis ranges from 52 to 77 kg N ha$^{-1}$ (Elkan, G. H. (1992).*Biological nitrogen fixation* . In: Encyclopedia of Microbiology. Ed: New York, Academic Press Inc. 1: 285-295).

Mixed Bacterial Inoculants

Mixed inoculants (combination of microorganisms) that interact synergistically can provide nutrients, remove inhibitory products and stimulate each other through physical or biochemical activities that may enhance some beneficial aspects of their physiology, like nitrogen fixation. An example of mixed bacterial inoculants is *Azosipirillum* which can associate with sugar- or polysaccharide-degrading bacteria (PDB), establishing a metabolic association where the sugar-degrading bacteria produce degradation and fermentation products used by *Azosipirillum* as a carbon source, which in turn provides PDB with nitrogen.

Other examples are the association between *Azosipirillum* and *Bacillus* that degrades pectin, *Azosipirillum* and *Cellulomonas* that degrade cellulose, and *Azosipirillum* and *Enterobacter coacae* that ferments glucose (Y. Bashan, (1998). Inoculants of plant growth-promoting bacteria for use in agriculture, Biotechnology Advances, 16: 729-770). *Azosipirillum* is also considered to be a *Rhizobium*-helper, stimulating nodulation, nodule activity and plant metabolism, all of which stimulate plant growth variables and plant resistance to unfavourable conditions. Beneficial combination of *Azosipirillum* or *Azotobacter* with Streptomyces and *Azosipirillum* with *Phialophora radicola* (fungal control agent) are documented.

Mixed inoculation with diazotrophic bacteria and arbuscular-mycorrhizal fungi creates synergistic interactions that may result in significant increase in growth, in the phosphorous content in plants, enhanced mycorrhizal infection and an enhancement in the uptake of mineral nutrients such as phosphorus, nitrogen, zinc, copper and iron.

Inter-cropping

Intercropping utilizes nature's integration technique in polyculture where the outputs from one plant is utilized by others. In intercropping, the productivity of the main crop is enhanced by the presence of added crops. The mechanisms of enhanced productivity of the primary crop through intercropping are numerous. Intercropping has been utilised successfully in non-mechanised agriculture. However, intercropping in modern mechanised agriculture is not always economical.

However, if the sole object of intercropping is the enhancement of biomass production and fertilizer reduction, then intercropping and mechanised agriculture can be sustainable. As we aim to enhance nitrogen fixation from air, intercropping of legumes with non-legumes in the presence of SSS can be highly successful. In the current intercropping techniques, transfer of nitrogen is across macroscopic scale (as opposed to several meters to centimetres in current practice) whereas, SSS technique can achieve nutrient transfer across microscopic scale, thus enhancing the effect of intercropping.

Plant Root/Water/Nutrient/Microorganism Interactions

The transport of bacteria and fertilizer to the plant roots through irrigation and/or diffusion results in the dispersion of the bacteria throughout the soil thus reducing the local bacterial concentration at the soil/root interface. Eventually both bacteria and soil are washed out of the reach of the root system. Furthermore, the continual dispersion of the bacteria can result in the breakdown of colonies, quorum signaling, collective activity and eventual bacterial depletion of the soil as a result of hostile soil environment. These events result in reduced probability of bacterial infection of the roots and the waste of fertilizer and water. Therefore, like water and nutrients/fertilizers, soil bacteria are also replaced using different strategies, including the coating of the seeds with a bacterial broth. Even at high bacterial concentrations, the interaction between the roots and bacteria are random as the root-bacterium interaction area per unit volume of the plant root region is small. The root surface area per unit volume of soil can be considered to be a Transport Area Density (TAD) which is important in many heat and mass transfer operations of biochemical and chemical processes which can be enhanced by increasing TAD. The current technique described herein brings together water, fertilizer, and where applicable bacteria and plant root within the pores of the SSS-polymer so that the effective diffusion path is reduced and the TAD is increased. Furthermore, the pores of the SSS-polymer act as a protective micro-environment for the micro-organisms while acting as water and nutrient source for the plant roots growing through its pores. Increased bacterial concentration enhances quorum signaling and enhances plant-bacterium symbiosis.

Further enhancement of mass transfer in biological or catalytic chemical reactions can be achieved by ensuring that all the catalytic sites are utilised, a strategy that requires the operations in monolithic bio- or chemical-reactors in which the catalytic/active sites are accessible through a network of hierarchic pores such as encountered in nature (lungs, liver, kidney, circulatory system etc). The so called 'Phenomenon Based Process Intensification' achieved in biological (including tissue engineering) and chemical systems represent intensification levels in the region of 10-1000 fold. In biological system, the intensification is achieved by the so called 'confinement' phenomena when the behaviour of matter or microorganisms is dependent on the size of the environment in which they are confined. Therefore, for a given microorganism, growth rate, selectivity, productivity can be controlled by using a support system with specific micro-architecture (pore size, interconnect size). The chemical/biological nature of the support system also affects microorganisms' behaviour. Therefore, based on the 'confinement phenomena', it is possible to intensify the biological processes. An important element of bioprocess intensification is to use nano-structured micro-porous materials with bioactive wall structure.

The use of nano-structured micro-porous polymers and bacterial constructs as soil additive results in the root penetration into the pores of polymer, growth of bacteria and rapid adsorption/slow desorption of water by the polymer. Plant growth (grass, jatropha, soybean and peas) and crop yield (peas) data (both fresh and dry yields) clearly indicate that this symbiotic system works well as bioreactor. Furthermore, plant growth intensification after each harvest also illustrates the growing contribution of these micro-(bio)reactors within the soil to plant growth as the nutrients are removed from the soil due to consumption and washing by water. This enhancement is due to the following attributes of the SSS-Polymer—bacterial constructs.

Water and nutrient (within water or provided by fertilizer adsorbed by the polymer) availability is enhanced because the SSS-polymer can readily adsorb water when available and slowly release when needed by the plant. Water transfer is no longer diffusion limited since the roots are within micrometers of the water source. In the case of bacterial association, the roots are also very close to the bacterium source and bacterial concentration remains high within the pores of the polymer.

The roots grow out of the polymer already infected and grow back into the soil where it can utilize water and nutrients, but requires no further nodulation.

As described below, depending on the chemical/physical structure of the SSS-polymer, the penetration of the bacteria from the soil can be prevented or enhanced. Prevention of undesirable bacterial penetration into the SSS-polymer bacterium constructs is partly because the bacterial concentration outside the polymer construct is small and there is no active mechanism (such as forced convection) present in the soil to promote bacterial penetration. The only mechanism is through bacterial motility and division. Furthermore, SSS-polymer excludes large or less motile bacteria from entering into the polymer construct, therefore, the existing bacteria within the pores are protected from the penetration and subsequent colonisation by the other bacteria.

SSS-polymer constructs also act as a sink for a sudden surge in toxins such as heavy metal ions (SSS-polymers when sulphonated become essentially an ion-exchange resin) or organic toxins. Cross-linked polystyrene-vinyl pyridine based SSS-polymers or sulphonated cross-linked polystyrene SSS-polymers used here are biphylic, that is, they adsorb both water or other solvents. Therefore, SSS-polymers can take up both metal ions and organic toxins which are subsequently released gradually as the toxin levels in the environment decrease or they are metabolized through phytoremediation or by bacterial degradation.

Current results detailed below indicate that even without the inclusion of bacteria into SSS-polymers, total biomass yield increases for all the plants tested. Nevertheless, in the case of leguminous crops, such as pea, and soybean both total biomass and crop enhancements are significant when the nitrogen fixing bacteria (*Rhizobium*) is present in the SSS-polymers in the absence of any water and nutrient stress. In the presence of water and nutrient stress, both non-biological and biological SSS-technique provides biomass enhancement compared with the controls. This clearly indicates that the pea plant receives more nitrogen through the SSS-polymers compared with the soil bacteria. This observation is further strengthened through the extensive presence of what appears to be plant exudates which provide plant/bacterium communication. Under normal conditions in soil-only growth, these exudates will be present in small concentrations and will be washed away from the root-bacterium interface. It is likely that these messenger chemicals increase plant nitrogen uptake. It has been found that the synthetic symbiotic system has a number of characteristics that enhance biomass/crop growth rate and yield.

According to the invention there is provided a plant growth support medium, the medium comprising a sulphonated polymeric material, having primary pores of size greater than 30 micron, the polymeric material being elastic to enable the pores to increase in size, for example due to water content or from penetration of a plant root.

The primary size of the polymeric material is preferably from 30-300 micron to provide a balance between void space and structural integrity for the material, and especially preferably from 50-150 micron.

Advantageously, the degree of sulphonation is from 40-75% and particularly advantageously from 60-70%. Too high a degree of sulphonation reduces the pore wall strength too greatly and too low a degree does not render the wall sufficiently elastic and hydrophilic.

Conveniently, the pore wall is also porous through the fusion of polymer grains in the size range of 10-20 nanometers. This nano-structure results in the formation of nano-pores (1-5 nanometers) thus permitting water, nutrient and metabolite transfer.

The polymeric material is advantageously selected from polystyrene, styrene/ethylhexyl acrylate copolymer or a styrene/vinyl pyridine copolymer. Particularly advantageously, the styrene/ethylhexyl acrylate copolymer has the components in a 75:20 weight ratio. Further particularly advantageously, the styrene/vinylpyridine copolymer has the components present in a 75:8 weight ratio.

Preferably, the polymeric material includes capillaries which are millimeters in size to facilitate plant root growth.

The primary pores are conveniently interconnected to allow water nutrients, bacterial and root hairs to grow from one pore to another.

Preferably, the walls of the pores are nano-structured in order to adsorb water and provide transport for water, air, nutrients and metabolites.

Conveniently, the polymeric material included in the SSS-polymer is elastic in order to allow root growth therethrough.

Preferably, the polymeric material is highly hydrophilic to allow rapid water adsorption but slow release of water.

Advantageously, the material is biocompatible or further advantageously bioactive to aid in promoting the growth of bacteria.

The SSS-polymer used preferentially herein is a nano-structured micro-porous crosslinked, ionic and hydrophilic polymer also known as PolyHIPE Polymer (PHP) with void volume in the range of 70-95%. They are either elastic before being rendered hydrophilic or they become elastic upon adsorption of water. Although these polymers can be produced with a primary pore size 0.5-300 micron, it is only the large pore grades which are preferred. If the formation of the coalescence pores (which can be several hundred microns in size) are allowed during polymerization, primary pore size can be reduced since the coalescence pores are dispersed into the primary pores. Note that the pore size increases when sulphonated PHP swells upon contact with water.

BRIEF DESCRIPTION OF THE DRAWINGS

The invention is now described with reference to the accompanying drawings. In the drawings:

FIG. 2(a-f) illustrate micro/nanostructure of a sulphonated PHP.

FIGS. 12(c,d,e,f,g) illustrate the effect of PolyHIPE treatment on the growth of plants.

FIGS. 21(a,b,c) show fungal growth on a spongy PHP (SNS-PHP) pore wall at different magnifications.

Figure 1A:
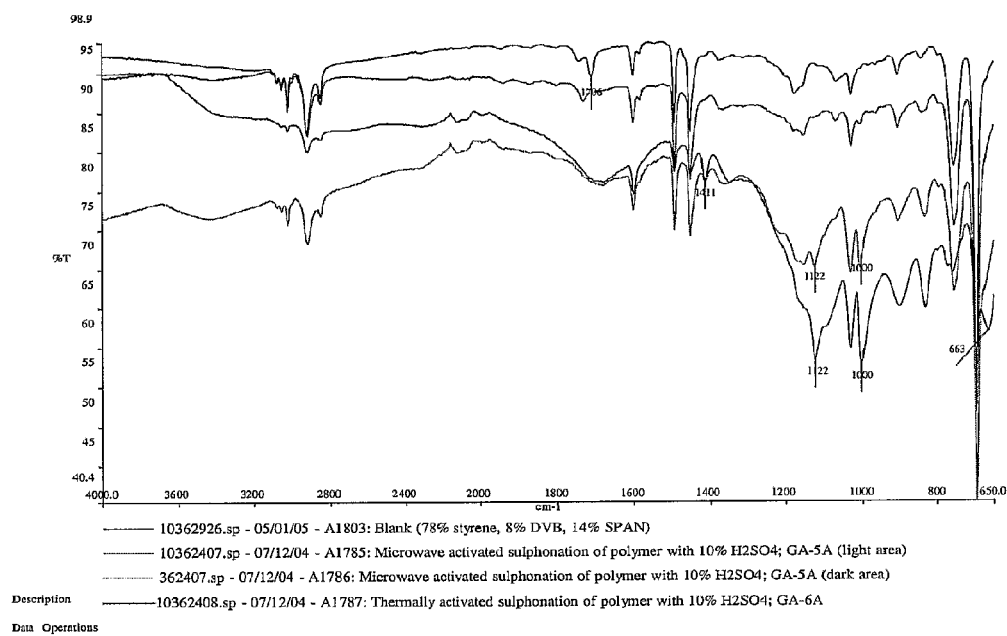
FIGS. 1(a, b). show Infra-red spectra of various sulphonated PHPs micro-wave irradiated without the washing procedure indicating sulphonation and carbon formation.

In order to achieve these characteristics, basic SSS-material were prepared and functionalized to achieve hydrophilicity, elasticity and fertilizer storage followed by inoculation with bacteria for biological nitrogen fixation and plant growth. These steps are summarized below.

The generic name for the nano-structured macro-porous polymer with interconnected pore is PolyHIPE Polymer (PHP) which is prepared through a High Internal Phase Emulsion (HIDE) polymerization route as disclosed in WO 2004/005355 (2004). The PolyHIPE Polymer used in these experiments consisted of 90% aqueous phase and 10% oil phase by volume.

The aqueous phase consists of deionised water, an polymerization initiator (potassium persulphate) and 5% sulphuric acid as the nano-structuring agent. The volume fraction of aqueous phase (phase volume) was 90%. Three types of polymers were prepared in which the oil phase composition is:
Monomer phase: Styrene=76-X-Y-Z %, where X, Y, Z have the following meaning
2-vinyl pyridine (2-VP)=X %
2-ethyl hexyl acrylate(2-EHA)=Y %
Oil phase soluble initiator (lauryl peroxide)=Z %
Cross-linking agent (divinyl benzene, DVB)=10° A
Non-ionic surfactant (sorbitan monooleate, Span 80)=14%

Since we can obtain satisfactory polymers without the use of oil phase soluble initiator, Z=0. Variation of X and Y led to the following 3 types of polymers. These are:
1) Cross-linked polystyrene (PS): X=Y=Z=0
2) Cross-linked styrene-ethylhexylacrylate copolymer (S-EHA CP): Y=20% X=Z=0
3) Cross-linked styrene-vinyl pyridine copolymer (S-VP CP): X=8% Y=Z=0%

The oil phase was mixed together at room temperature. The oil phase was placed into the mixing vessel (internal diameter 12 cm) just before the start of the emulsification and then the aqueous phase was dosed into the oil phase, via a peristaltic pump, whilst mixing occurs. Mixing was achieved via 3 flat paddles (9 cm diameter), stacked at right angles. The bottom impeller was utilized as close to the bottom of vessel as possible and the other impellers were spaced 3 cm apart so that when all of the aqueous phase was dosed, the top impeller was immersed 1 cm below the emulsion surface in the mixing vessel.

The dosing time was $t_D$ and the impeller speed was $\Omega_D$ during dosing. After the completion of dosing, the emulsion was homogenised by mixing for a period of $t_H$ at a rotational impeller speed of $\Omega_H$ rpm. Depending on the oil phase composition and the desired pore size (D), these values were changed. The interconnect hole size (d) is mainly dictated by aqueous phase volume ($\Phi$) as well as the oil-phase composition and the type of surfactant used. The volume of the oil phase was 25 ml and that of the aqueous phase 225 ml.

For a given oil phase—aqueous phase composition, the pore and interconnect sizes in the micro-porous polymer was achieved mainly at the emulsification stage (i.e., PHP pore size=dispersed phase droplet size in HIPE) provided the emulsion was stable during polymerization. Droplet size in HIPE is determined through the control of temperature of emulsification ($T_E$), mixing speed ($\Omega_D$ and $\Omega_H$), dosing and mixing times ($t_D$ and $t_H$) as well as the impeller size and type. If the emulsion is stable, pores of PHP are termed as primary pores (see: G. Akay, S. Dawnes, V. J. Price-Byron, Microcellular polymers as cell growth media and novel polymers, EP 1183328 A2 (2002); US 09, 856,182 (2002); G. Akay, M A Bokhari, V J Byron and M. Dogru, Development of nano-structured materials and their application in bioprocess-chemical process intensification and tissue engineering. Also in Chemical Engineering Trends and Developments, Ed: M A Galan and E. M. Del Valle, Wiley, London, 2005. Ch. pp. 171-196. (2005)). If the emulsion becomes unstable during polymerization, primary pores start to coalescence which results in the enlargement of the pores. These enlarged coalescence pores are dispersed in the primary pores and their volume fraction and size increases with the degree of instability and size of the primary pores. Although the ratio of d/D is relatively constant for PHP with primary pores, for coalescence pores, the distribution of d/D is very broad. For the purposes of the present invention polymers having a primary pore size of >40 microns have been found to be effective and those having a primary pore size of from 30-200 microns especially effective, with 50-10 micron particularly effective.

The high internal phase emulsion (HIPE) was polymerized at 60° C. for 8 hours in polypropylene cylindrical tubes (2.3 cm diameter) with caps. After polymerization and formation of a solid polymer, any required functionalized can be carried out. In the polymeric materials of the present application, high water adsorption capacity and elasticity are required. Elasticity can be achieved either by the presence of ethylhexyl acrylate in the copolymer chains (i.e., PS-EHA Copolymer) or by swelling upon water adsorption when cross-linked styrene is transformed into highly hydrophilic polymer by sulphonation. When water is removed from sulphonated PHP, polymer returns back to its original volume. Although PS-EHA PHP is elastic it is also hydrophobic. Such a polymer can be rendered hydrophilic by sulphonation.

After polymerization, PHP samples were cut into ca. 4 mm disks and were then washed with distilled water for 2 hours in excess water while changing water every 30 minutes. PHP disks were dried in a fume cupboard for 24 hours before sulphonation. The sulphonation and neutralization of the polymers was carried out by one of the methods described below.

Method 1:

After polymerisation, washing and air drying as described above, polymer disks were soaked in 97% w/w sulphuric acid for a period of 2 hours. In order to obtain elastic sulphonated PHP which swells and takes up large amounts of water (typically 18 times of its own weight when 90% void PHP is used) it is preferable to wash the polymers before the adsorption of the concentrated sulphuric acid and subsequent microwave irradiation. These polymer samples containing 97% acid were then irradiated with microwaves using a Panasonic™ kitchen microwave oven (1000 W). Less concentrated acid can be used but the irradiation time needs to be increased in this case. However, microwave ovens are well known for their irregular distribution of irradiation, which usually results in the development of hotspots within the sample. Hotspots can lead to charring of the polymer, so as a quality control measure, the samples were irradiated at intervals of 30 seconds after which the discs were allowed to cool for 60 seconds and were turned upside down and randomly distributed into new positions on the microwave dish. Irradiation was stopped every 30 seconds and samples were reversed on the microwave oven and irradiation was continued until total irradiation time was typically 150 seconds for 14 polymer discs. Under these conditions, the degree of sulphonation was 70%. Prolonged exposure to sulphonation conditions does not enhance the degree of sulphonation but increases elemental carbon formation. Therefore, this irradiation time at this power rating was found to be optimum. During microwave irradiation, as the sulphonation proceeds, PHP polymer disks become visibly swollen and they appear elastic.

It has been found that a degree of sulphonation of from 40-75% is suitable for the present invention. A value of below 40% leads to walls of insufficient elasticity and water adsorption capacity, whereas values of greater than 70% give walls which do not have sufficient integrity. A degree of sulphonation of from 60-70% has been found to be especially preferable. The elasticity of the walls enables the pores to swell in size on, for example, root penetration. Moreover, the sulphonic groups on the pore walls are hydrophilic, and so attract or retain water. Again the elasticity enables more water to be held within a pore and hence the polymeric material of the plant growth medium. It is to be noted that the walls of the primary pores typically have a thickness of 0.1-1.0 nanometres. Moreover the walls can be of a fused granular nature enabling passage of water through the gaps between adjacent granules. A granule size of from 10-20 nanometres has been found by scanning electron microscopy.

When micro-wave irradiation is carried out on industrial scale, a moving tray is used with an irradiation—no irradiation cycle with air circulation.

After sulphonation, polymeric samples were washed thoroughly with water to remove excess acid and subsequently it was neutralized using 5.0N ammonium hydroxide solution followed by further water cleaning until the solution was pH 5.5. These polymers were dried, and stored for future use. There is a slight increase in the thickness of the sulphonated PHP disks even after drying (i.e., thickness increases from 4 mm to ca. 5 mm). Some of the disks were cut into cubes measuring approximately 5×5×5 mm.

Method 2:

A mixture of concentrated (97%) sulphuric acid and nitric acid was used for sulphonation. The volumetric concentration of sulphuric acid in nitric acid ranged from 90% to 10%. This has the advantage of neutralizing the sulphonated PHP with ammonium hydroxide to obtain a nitrogen rich fertilizer within the pores of hydrophilic polymer.

The level of sulphonation is controlled to give a polymer with the desired characteristics. Due to the presence of the sulphonic acid or sulphonate groups the surface of the polymer becomes more hydrophilic causing water to build up on the surface. Where the build up occurs within one of the pores, the pores become filled with water. In addition the sulphonation imparts elasticity to the walls enabling the water containing pores to swell up to seven times their original size. The polymer therefore acts efficiently to retain water, along with any salts contained therein. This fix allows the polymers to retain water and release it slowly, a characteristic which enables the polymer to be of great use in releasing water to a plant in arid conditions.

Typical sulphonation levels are from 40-75% with 60-70% being a preferable range.

It is to be noted, that the wall thickness of a pore tends to be greater for pores of larger size. Moreover, in some embodiments, the walls are of a granular nature having a grain size of from 10-20 nm. The grains do not pack together to give a completely sealed wall but instead, gaps are left between grains which allows water and dissolved salts to pass therethrough.

In order to produce a biologically active synthetic symbiosis system containing a bacterial dispersion for the inoculation of sulphonated PHP the following method was used.

The *Rhizobium leguminosarum* were supplied in a vacuum dried form. To prevent contamination of the samples, the entire process of preparing the *R. leguminosarum*, from the initial opening of the bacteria container to inoculation of the plates, was carried out within a sterilised fume cupboard. To disperse the dried pellet of *Rhizobium*, 5 ml of the broth medium was added to the pellet and left to equilibrate for 30 minutes. A sterile loop was then placed into the bacterial dispersion and streaked across the prepared agar plate to produce isolated colonies during incubation. A fresh sterile loop was used for each agar plate, which was kept sealed immediately before and after inoculation. The plates were then stacked, labeled and sealed with two strips of adhesive tape crossing over the top and bottom of the pile. The dishes were placed upside down (to prevent condensation from falling onto the plates) within an incubator set to 26° C. and left to allow the *R. leguminosarum* to grow for 7 days until clear individual colonies had developed. A selection of individual colonies were then inoculated onto fresh plates and incubated again, to ensure that no contaminants had got onto any plates.

From the second set of incubated plates, a single colony was collected on a sterile loop and placed into one of the five different containers of 100 ml autoclaved broth medium. The containers were then placed into a shaker and rotated at 160 rpm for 72 hours at a temperature of 26° C. After shaking, the broth was stored in sterile 50 ml tubes at −18° C. until required, at which point they were defrosted at room temperature for 5 hours.

Sulphonated polymer disks were dried, and stored for future use as described previously.

Some of the disks were cut into cubes measuring approximately 5×5×5 mm. These materials were used in soil with or without bacterial inoculation.

Some of the polymer disks had capillaries going through them. These capillaries can be produced in 1-, 2- or 3-dimensional network using the technique described in (Akay et al, WO 00/34454).

In another case, cross-linked polystyrene is chopped into small particle (size range 100-2000 micron), washed to remove residual monomer and surfactant followed by sulphonation and neutralized and dried. These materials were used to test the effectiveness of the physical form of the NSMP Polymers as soil conditioners. The use of particulate form of sulphonated PHP enhances the polymer-plant root interactions. When preparing sulphonated SSS-polymer containing bacteria, the following method was used.

The *Rhizobium* growing broth medium was prepared using the method and ingredients recommended by the supplier of the bacteria, described here. Firstly, 200 ml of soil extract was prepared by collecting and sieving 80 g of air-dried soil through a 2 mm sieve, and mixing it with 0.2 g of sodium carbonate and 200 ml of deionised water. The extract was then autoclaved for one hour at 121° C. to ensure sterility, and then stored at room temperature. The growing medium was prepared as a liquid broth, and also with the addition of agar, as a solid media. For 500 ml of broth media, 400 ml of deionised water was mixed with 100 ml of the soil extract, 5 g of Mannitol and 0.5 g of yeast. The resulting solution was then equally separated into 5 different 100 ml containers and autoclaved. To prepare the solid agar medium, the above procedure was followed but an additional 7.5 g of agar was added prior to autoclaving. After autoclaving, the agar medium was poured into sterilized Petri dishes within a sterilized fume cupboard, and allowed to cool and set for 30 minutes before being stacked and stored whilst the bacteria were prepared.

The total weight of soil within the filled pot was 900 g. Only the 5×5×5 $mm^3$ version of the spongy PolyHIPE Polymer was used in these experiments, and it was only applied to the bottom 25 mm of soil (i.e. below the seed) at a 0.5% w/w dose, equaling 1 g of polymer within 200 g soil. The polymer was soaked in 25 ml broth until absorption equilibrium was reached, and then thoroughly mixed into the soil below the seed.

John limes Loam-Based Compost No. 3 was used for soil: Horticultural sand was supplied by Moorbank Gardens, Newcastle. Perennial rye grass used was of the Superstar Variety and purchased as seeds from Agriculture, Environment and Fisheries Department, UK. Fertilizer, Nitram was supplied by Terra Nitrogen, Teeside, UK. Nitram contains 34.5% nitrogen, and the applied dosage was dissolved into 25 ml water given to each pot at the planting stage. Also used was the commercially available liquid fertiliser Miracle-Gro® Pour & Feed, produced by The Scotts Company (UK) Limited, in Godalming, Surrey, UK. The Miracle-Gro® (MG) fertiliser was used as per the manufacturer's guidelines, with each pot receiving an undiluted application of 25 ml at the planting stage. Neither Nitram nor Miracle-Gro® was reapplied after the initial planting.

Only the 5 mm size cubes of the sulphonated spongy PHP (SNS-PHP) were used in these experiments, and it was applied at a 0.5% w/w dosage into the soil. The polymer was microwave sulphonated and pH adjusted to pH 5.5 to match that of the soil, using the methods described previously. The polymers were mixed into the soil when dry so that they could absorb water and/or fertiliser as they were poured over the soil.

Agar, Mannitol, Yeast, and Sodium Carbonate were all obtained from Sigma Aldrich, Gillingham, Dorset. Bacteria (*Rhizobium leguminosarum*) was obtained in vacuum dried form from Deutsche Sammlung von Mikroorganismen and Zellkulturen GmbH (DSMZ), Braunschweig, Germany. Perennial rye grass used was of the Superstar Variety and purchased as seeds from Agriculture, Environment and Fisheries Department, UK. Peas (*Pisum sativum* L.) were the Kelvedon Wonder, dwarf versatile variety, supplied by Johnsons of Newmarket, Suffolk, UK.

Grass and pea were used as the two test plants to test the effectiveness of the synthetic symbiotic systems developed in this work.

In order to plant the grass, horticultural soil was mixed with 25% horticultural sand and 200 g of the resulting mixture of soil was placed into 8 cm diameter pots. The soil was 6 cm deep in the pot and reached the lower lip of the pot, where the diameter was 7 cm, the surface area 38.5 cm$^2$, and was 1.5 cm below the upper lid of the pot. 0.5% w/w polymer was thoroughly mixed into the soil before the addition of 5 g of perennial rye grass seed which was spread evenly over the soil surface. A control treatment without polymer was also used. The seeds were covered with a thin layer of soil until level with the lower lip of the pot, and then given 40 ml of tap water. The pots were randomly distributed within a 2×2 m$^2$ area of greenhouse. The felt mat on which the pots stood was kept moist throughout the day. After 21 days the grass was cut at the upper lip level of the pot, 1.5 cm above the soil surface. The grass was then immediately weighed to determine the fresh weight before being placed in an oven at 60° C. for 72 hours and reweighed to determine the dry weight. Growth experiments were continued for another 21 days and the second grass harvest was obtained by cutting the grass and treating the yield as in the first harvest. The third and final harvest was obtained after another 21 days at the end of which remaining grass and roots were removed from the pots and carefully washed in water in order to reveal the SNS-PHP root interactions.

The following types of PHPs and watering regimes were used in greenhouse grass growth experiments.

Sulphonated-Neutralized-Spongy PS-PHP (Referred to as Spongy PHP and Denoted by SNS-PHP)

Physical Forms:
a) Cubes measuring 5×5×5 mm
b) Powder (powder size 100-2000 micron)
c) Cubes measuring 5×5×5 mm with at least one continuous capillary (capillary size: 2 mm)

Sulphonated-Neutralized-Elastic PS-EHA-PHP (Referred to as Elastic PHP and Denoted by SNS/EHA-PHP)

Cubes measuring 5×5×5 mm

Sulphonated-neutralized-Spongy PS-VP-PHP

Cubes measuring 5×5×5 mm were prepared from polystyrene-vinyl pyridine PHP followed by neutralization with ammonium hydroxide and subsequent washing to bring the pH=5.5.

Preparation for Pea Planting

In order to prepare for pea planting a soil mixture was 7.5 cm deep was formed which the lower lip of the pot, 2 cm below the upper lid of the pot. The total weight of soil within the filled pot was 900 g. 5×5×5 mm$^3$ blocks of the spongy PolyHIPE Polymer were used in these experiments, and applied only to the bottom 1 inch of soil (i.e. below the seed) at a 0.5% w/w dose, equaling 1 g of polymer within 200 g soil. The polymers had been microwave sulphonated and pH adjusted to pH 5.5 to match that of the soil, using the methods described above. A control treatment without polymer was also used.

In the case of the uninoculated peas, the polymers were applied to the soil when dry. For the inoculated pots, 25 ml of the bacterial broth was applied directly to the soil for the control, or for the polymer treatment, the polymer was soaked in 25 ml broth until absorption equilibrium was reached, and then thoroughly mixed into the soil below the seed. The remaining, unabsorbed broth was then poured over the soil around where the seed was to be planted. One pea seed was placed in the centre of each pot on 1 inch deep soil, then covered with a further 2 inches of soil. All pots were then given 50 ml water and randomly distributed within a 2×2 m$^2$ area of greenhouse.

During the experiment all pots were kept moist by daily watering. After 42 days the shoots were cut at the base, and the pea pods were removed and kept separate from the rest of the stein and leaves. The yields of the pea pods were measured separately to the rest of the shoot biomass (stems and leaves), to allow for a comparison between crop yields as well as the total (i.e. stem and pods) biomass yields. The pea pods and stems from each pot were stored in labeled, sealable plastic bags and then immediately weighed to determine the fresh weight. Once the fresh weight of each sample was recorded, the samples were placed in an oven at 60 C for 72 hours and then individually reweighed and recorded to determine the dry weight. Four replications were used for each treatment.

Watering Regime

For grass growth, three different watering schedule were used: 1) Daily watering; 2) Weekly watering (Semi-arid conditions, with 40 ml water per week per plant pot); 3) Reduced weekly watering (Arid conditions; 20 ml water per week per plant pot). For pea, clover and jatropha only one watering schedule was used.

Statistical Analysis of Plant Yield Data

The mean fresh and dry weights for each harvest were plotted into bar charts. The mean yields were compared using two sample t-tests of independence assuming equal variance at 95% confidence, and confirmed using a one-way analysis of variance with a Tukey's Pairwise Comparison. All greenhouse experiments were done in quadruplicate.

Materials Characterization

The SSS-polymers were characterized firstly by FT-Infra Red spectroscopy to detect the chemical differences between different types of polymers prepared. In all cases, PHPs were washed before FT-IR measurements. FT-IR spectra of several PHP samples after polymerisation and sulphonation are shown in FIG. 1(a,b). The data indicates the presence of elemental carbon in micro-wave irradiated samples (FIG. 1(b)).

Specific surface area measurements were carried out using a Beckman Coulter (Palo Alto, Calif.) SA3100 BET Gas Adsorption Surface Area Analyser to assist in determining the water absorption capacity. Surface area measurements were conducted after each stage of preparation using washed samples (i.e., after polymerization, sulphonation and neutralization). Like the spongy PHP, the elastic PHP contained 5% acid in the aqueous phase and had a phase volume of 90%. Elastic PHP was prepared using a variety of sulphonation techniques.

which time the PBS was drained away. Once the sample had been washed, the process of fixing the bacteria began. Next, a solution containing 2% Glutardialdehyde diluted with PBS was poured over the sample until it was covered, at which point the container was sealed and left at room temperature for a period of 24 hours. After 24 hours, the samples were given a final wash in PBS for 10 minutes to remove any debris and complete the fixation process.

The samples needed to be preserved until examined under the SEM, and this was achieved via dehydrating using ethanol. Dehydration was achieved by first immersing the sample in 10% ethanol for a period of 10 minutes. After the 10 minutes, the ethanol was drained off and the sample was immersed in 25% ethanol for a further 10 minutes. The process was then repeated with 50 and 75% ethanol, and then the sample was stored in 100% ethanol at 4 C. Before examination under SEM, the samples are critically point dried and coated with conductive material (carbon, gold or gold alloy) using a sputter coating equipment under vacuum.

Samples were mounted on circular discs with 3 mm cylindrical rods coming off of the bottom, and fixed in place using

TABLE 1

Water adsorption characteristics of various sulphonated - neutralised PolyHIPE Polymers as a function of processing conditions.

| Type of Sulphonated PHP | Preparation for sulphonation | Water absorption capacity after 1 minute (g/g) | Equilibrium water absorption capacity (g/g) | Nominal pore size (μm) |
|---|---|---|---|---|
| Rigid crosslinked sulphonated - neutralized styrene homopolymer (SNS-PHP) | Washed and dried before acid adsorption | 8.3 | 8.4 | 20 |
| Spongy crosslinked sulphonated- neutralized styrene homopolymer (SNS-PHP)-Spongy PHP* | Washed and dried before acid absorption | 18.1 | 18.1 | 150 |
| Elastic crosslinked sulphonated - neutralized polystyrene-ethylhexyl acrylate copolymer (SNS/EHA-PHP) | Immediate adsorption of acid, no washing | 12.3 | 12.5 | 90 |
| Elastic crosslinked sulphonated- neutralized polystyrene-ethyl hexylacrylate copolymer (SNS/EHA-PHP) - Elastic PHP* | Washed and dried before acid adsorption | 15.9 | 18.8 | 90 |

*PHPs used in greenhouse experiments
To reduce costs and time required, the elastic polymer used in plant growth experiments was prepared for sulphonation with immediate acid absorption (i.e. no washing) and hence had a water uptake capacity of 12.5. Spongy SSS polymer (SNS-PHP) adsorbs water very rapidly compared to polystyrene-ethyl hexyl acrylate copolymer which is elastic even before sulphonation and coded as SNS/EHA-PHP).

Scanning Electron Microscopy (SEM) Studies

SEM equipped with EDX analysis was used to measure the average pore and interconnect sizes of Poly HIPE polymers using low magnification images. Two types of samples were fixed and examined under the SEM, the first being inoculated polymers used in the greenhouse experiments and hence placed into the soil with the seeds, and the second being polymers that had simply been autoclaved after sulphonation and then placed into an incubator with the bacterial broth. The latter was prepared so that a clean sample could be examined for growth of microorganisms (Rhizobium leguminosarum or Mycorrhizal fungi) without potential contamination from native soil bacteria. It was prepared by soaking the polymer in the bacterial broth and leaving it in an incubator at 26° C. for a period of 7 days. Both types of sample were washed and fixed using the same method, as described below. However, for Rhizobium, preferred growth period is 3 days when the stationary period is reached.

Before fixing the R. leguminosarum inoculated within the polymer, the sample must be washed in a new container using Phosphate Buffered Saline (PBS). PBS was poured over the sample until it was completely immersed. The sample remained immersed in a sealed container for 10 minutes, after a conductive adhesive tape (usually a graphite based carbon tape), or in the case of smaller or uneven samples, grounded to the mount using dried silver paint. Great care must be taken not to disturb the surface of the sample, and in the case of cross sections of the sample, it must be cracked to avoid damage from the cutting process.

The fracture surfaces of the samples were gold coated under vacuum before SEM examination. Pore size was measured by measuring the pore diameter on the SEM micrographs and number average size recorded after correcting them to take into account of the random fracture nature of the fracture surface.

FIG. 2(a,b,c,d,e,f) illustrate the typical micro/nano-architecture of the sulphonated PHP (phase volume 90%) samples before and after neutralization. FIG. 2(a) shows a large coalescence pore (size 250 micron) surrounded by smaller primary pores (size ca. 75 micron) at low magnification. It also shows the usual open pore structure of PHP after polymerization, sulphonation and neutralization stages respectively. The pore size is not affected by the chemical modification of the samples. FIG. 2(b) shows the fine structure of the wall surface and wall interior which are further illustrated in FIGS. 2(c) and 2(e) respectively. FIG. 2(e) shows the primary pores (size 70 micron) of the sample illustrated in FIG. 2(a) after neutralization (SNS-PHP). Surface structure of this SNS-PHP is shown in FIG. 2(f) which illustrates that the surface voidage is reduced compared with the sulphonated un-neutralized (acid form) polymer.

Scanning Electron Microscopy of Bioactive NIP with Bacteria and Plant Roots

Some of the PHP samples were used to cultivate bacteria and subsequently used in soil for nitrogen fixation as well as for soil conditioning. In both cases plant roots penetrate into the sulphonated spongy PHP and therefore the interactions between PHP+plant as well as between PHP+bacterium+plant could be studied by examining the fracture surface of the PHP. Plant root penetration was also observed with the elastic PHP which potentially may also be used for cultivating bacteria and hence was also examined under SEM. Due to the presence of the biological components within the spongy and elastic PHPs, a different SEM sample preparation technique was used. When investigating the samples containing plant roots and/or bacteria, biomaterial associated with PHP was first fixed and subsequently coated with carbon as described above.

The association between spongy neutralized PHP and grass root was determined. Sulphonated neutralized spongy PolyHIPE Polymers (SNS-PHP) were used as soil additive throughout. It was used in the form of cubes measuring approximately 5 mm×5 mm×5 mm. At the end of the 63$^{rd}$ day growth period, following the cutting off the grass, roots were washed and photographed.

Figure 3:
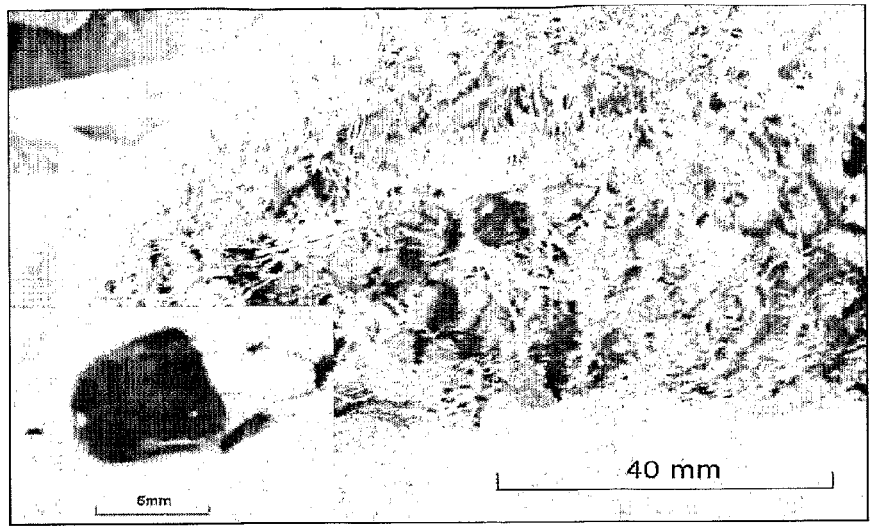
FIG. 3 shows grass root association when 0.5% w/w ca. 125 mm$^3$ spongy neutralized PolyHIPE Polymer (SNS-PHP) was used in the soil as soil conditioner with daily watering.
Figure 4A:
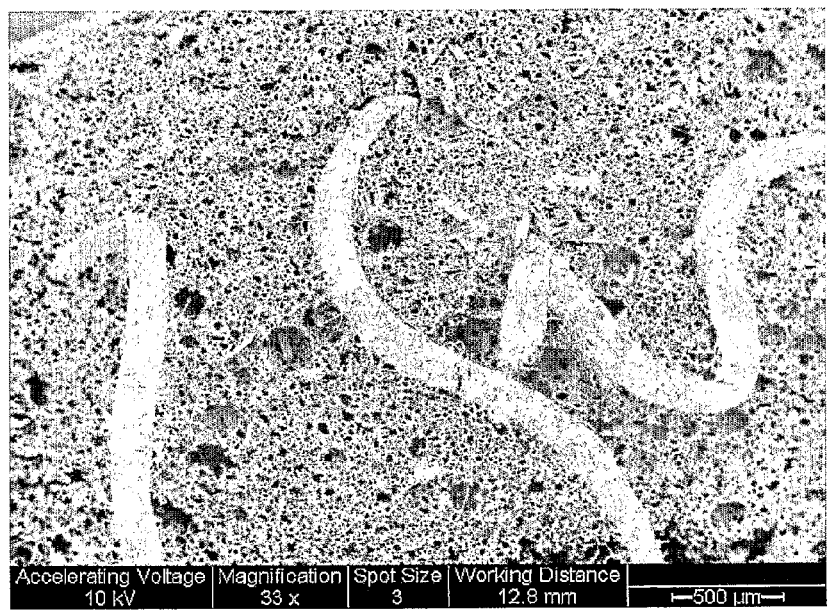
FIG. 4(a) is an SEM of the SNS-PHP surface showing the presence of the primary grass roots growing through the spongy neutralised PolyHIPE Polymer structure.
Figure 4B:
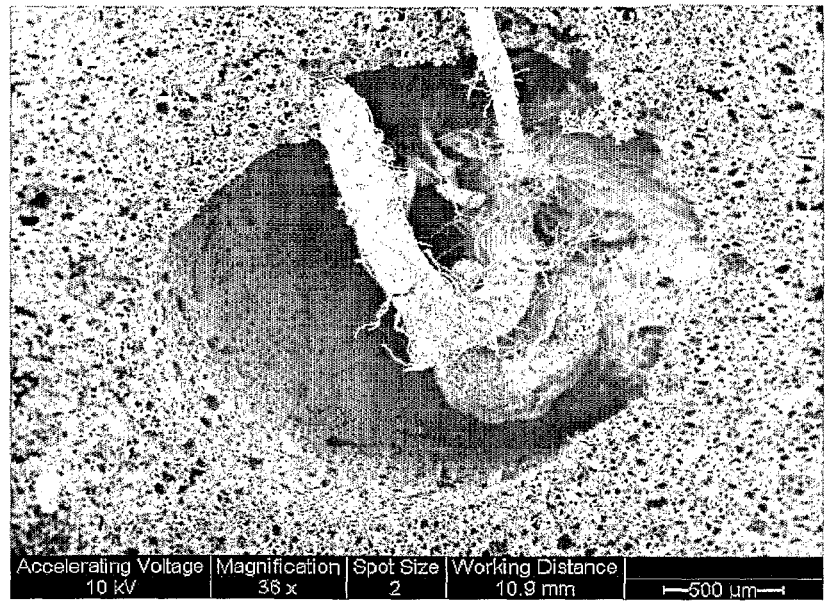
FIG. 4(b). SEM of the SNS-PHP (Spongy polymer) surface showing the presence of fine root hairs coming out of the capillary present in the SSS-polymer.
Figure 4C:
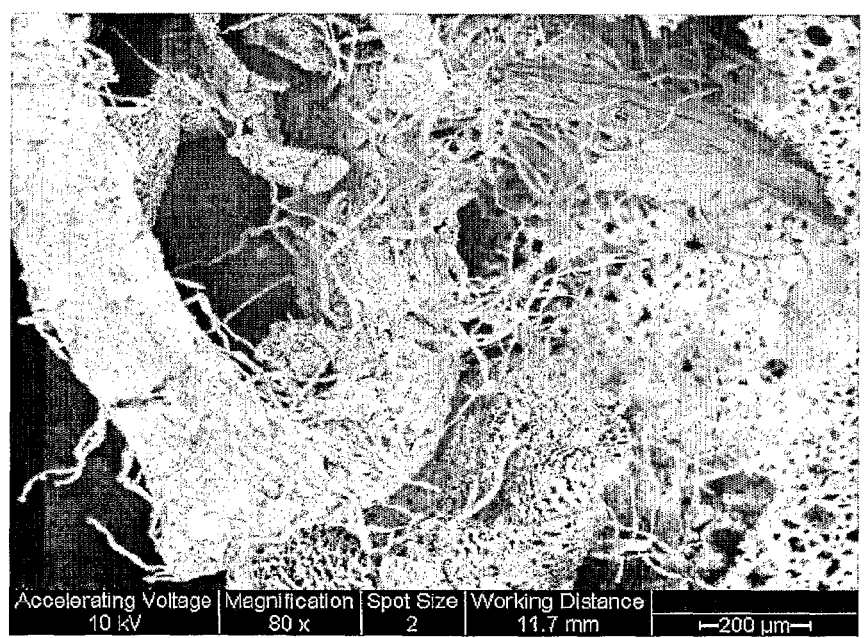
FIG. 4(c): Same as FIG. 4(b) at higher magnification.
Figure 4D:
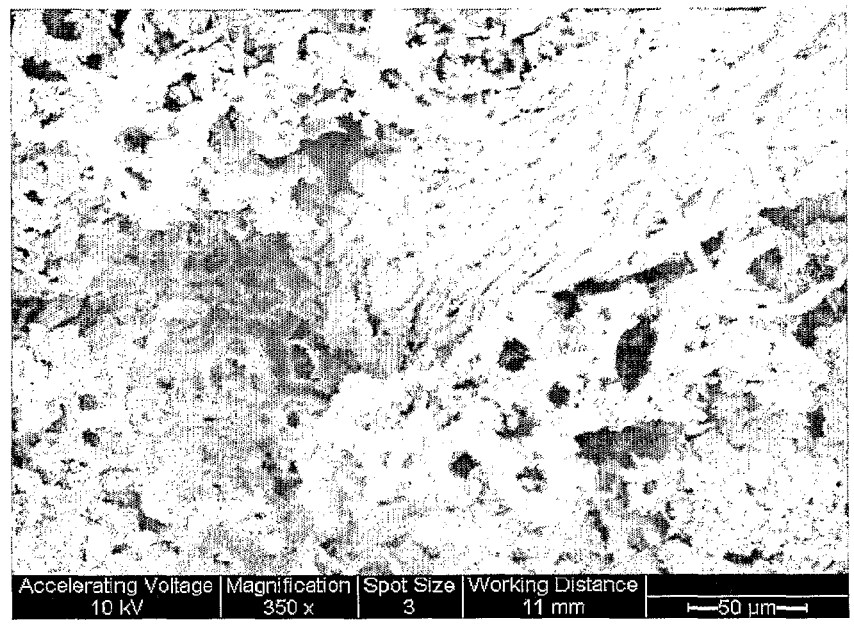
FIG. 4(d): Grass root growing through SSS-polymer structure.
Figure 4E:
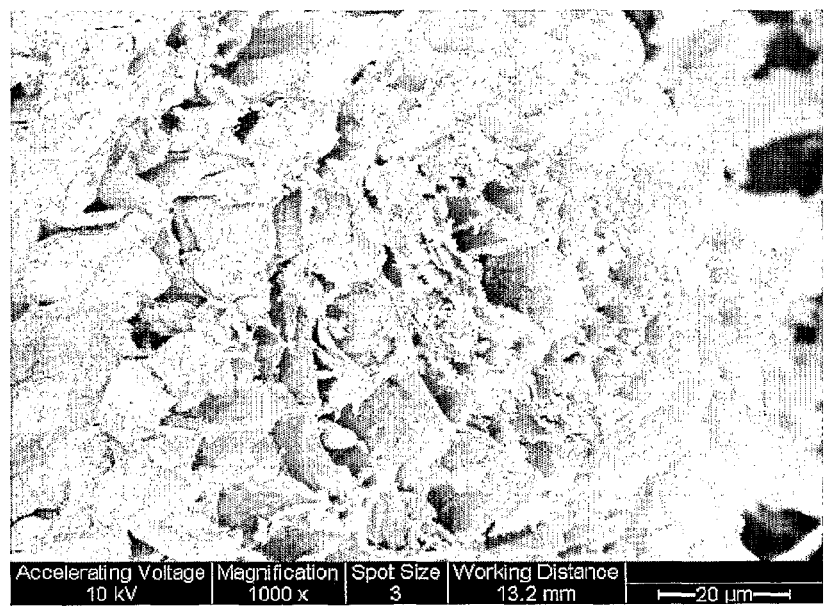
FIG. 4(e): Detail of grass root structure within the spongy PHP (SNS-PHP).

As shown in FIG. 3, the roots penetrated the polymer structure so that they remained even after rinsing the soil away from the roots with water, and lifting up the entire root network by just holding onto a few grass shoots. The roots were observed to not only attach to the surface of the polymer chunks, but actually grow through the structure so that it became an intricate part of the root network. This phenomenon was more closely examined under SEM (FIG. 4(a,b,c,d,e)) and it was clear that not only root hairs but also the primary roots were travelling through the polymer.

As seen in FIGS. 3 and 4, SNS-PHP not only contains fine root hairs (diameters of ca. 10 μm) which can pass through the interconnecting holes but also primary roots with diameters of 150 μm comparable to the size of the pores. This indicates that when the primary roots grow from the root hairs within the polymer, they can distort the polymer to make way for the growing root as the polymer is spongy and capable of swelling. All blocks of PolyHIPE are associated with roots at the end of the growth experiment. This extensive root association clearly indicates that the roots are directed towards the source of water (i.e., SNS-PHP).

Figure 5A:
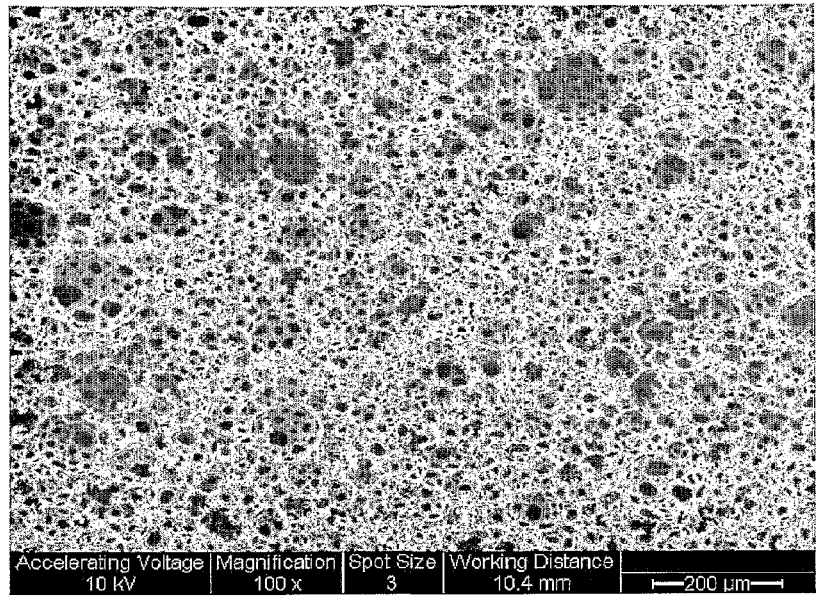
FIG. 5(a): Low magnification SEM of elastic sulphonated PHP (not neutralized) before use in soil.
Figure 5B:
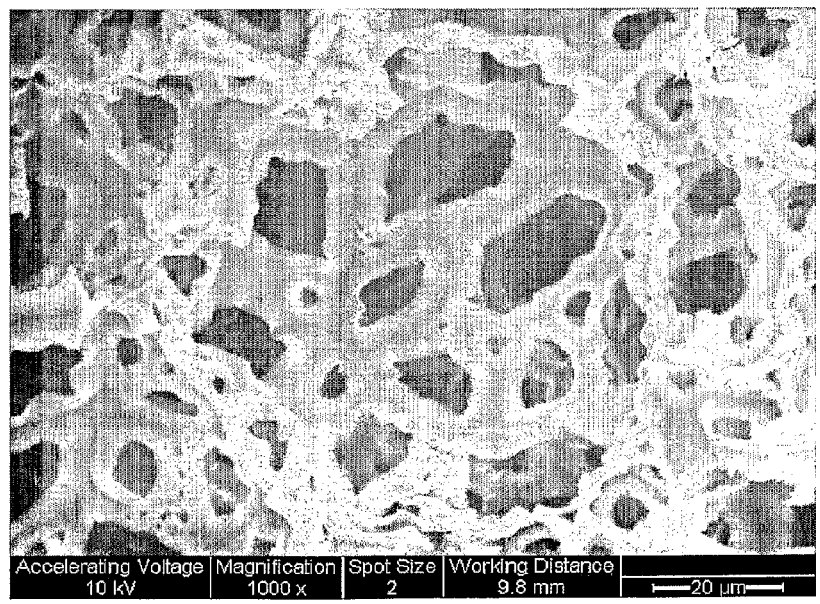
FIG. 5(b): SEM of elastic sulphonated PHP (not neutralized) at higher magnification showing the structure of the pores and interconnects.
Figure 5C:
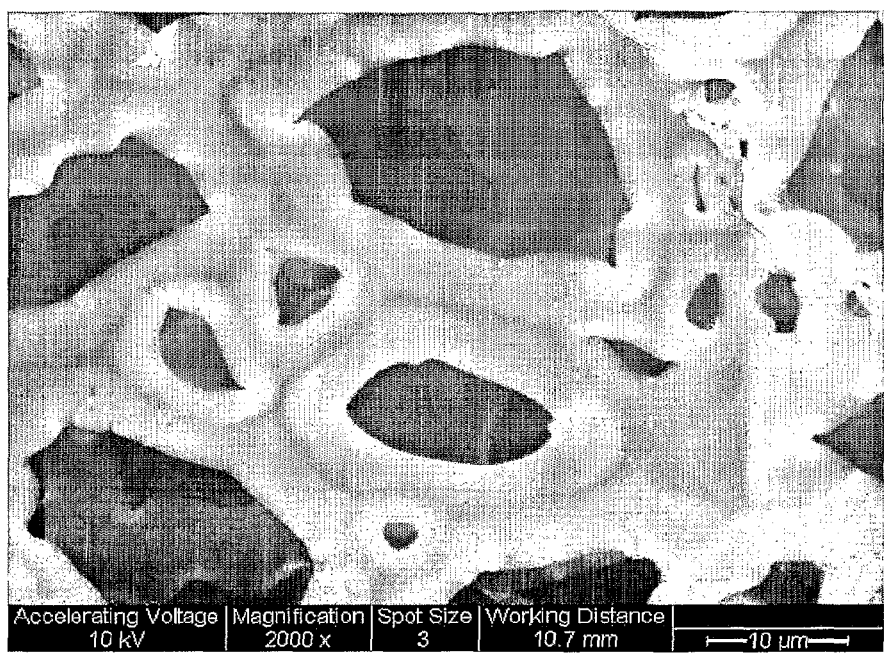
FIG. 5(c): Same as in FIG. 5(a) at higher magnification showing the wall structure.
Figure 6A:
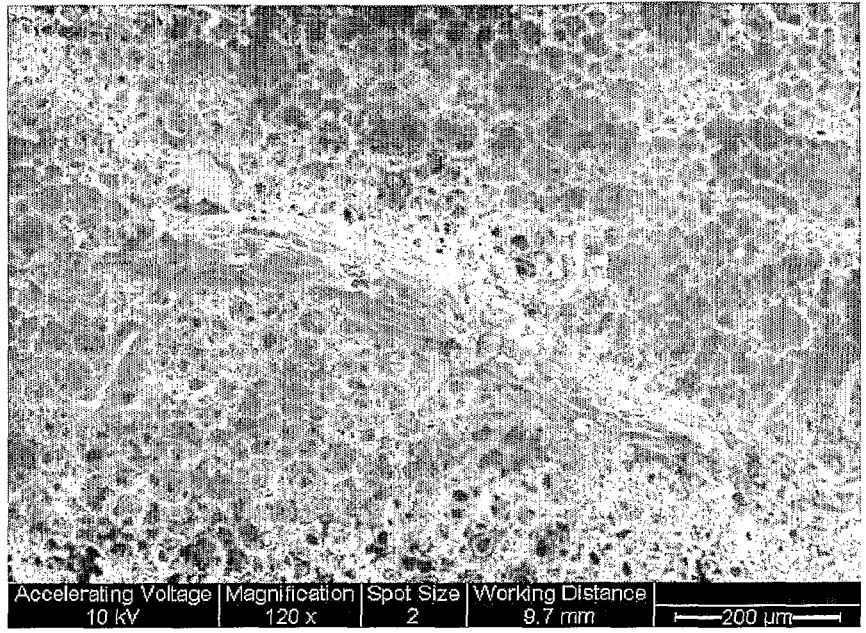
FIG. 6(a): SEM of neutralised elastic PHP (SNS/EHA-PHP) with grass root association (cross section).
Figure 6B:
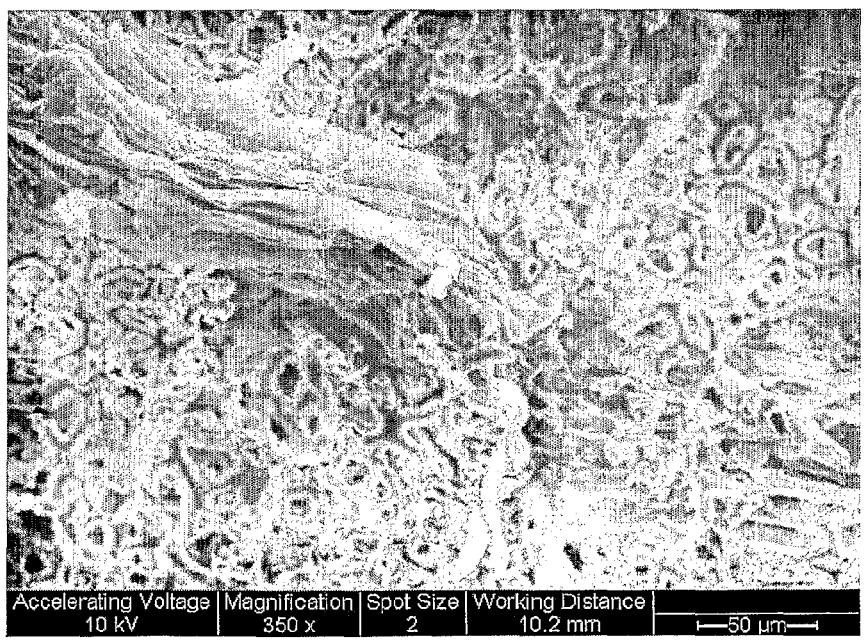
FIG. 6(b): SEM of sulphonated-neutralised elastic PHP (SNS/EHA-PHP) with grass root association (cross section).

Further trials with the elastic version of PolyHIPE (FIGS. 5(a,b,c)) also demonstrated plant root associations with the polymer (FIGS. 6(a,b)).

Using Nitram™ ammonium nitrate (AN) as well as Miracle-Gro® (MG) fertilisers, it was possible to investigate whether PolyHIPE Polymer based slow release fertilisers can increase yields of grass via improved fertiliser use efficiency. Each slow release fertiliser treatment used was compared against a control without polymer or nutrients, as well as an equal fertiliser treatment without polymer.

The Nitram™ contained 34.5% nitrogen, and the applied dosage (0.1 g) was dissolved into 25 ml water given to each pot at the planting stage. Also used was the commercially available liquid fertiliser Miracle-Gro® Pour & Feed, produced by The Scotts Company (UK) Limited, in Godalming, Surrey. The Miracle-Gro® (MG) fertiliser was used as per the manufacturer's guidelines, with each pot receiving an undiluted application of 25 ml at the planting stage. Neither Nitram™ nor Miracle-Gro® was reapplied after the initial planting.

Figure 7A:
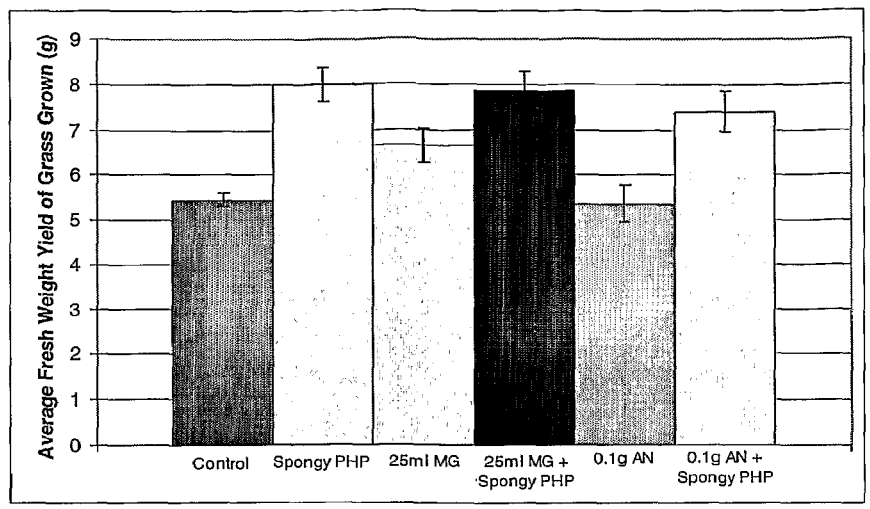
FIG. 7(a): Effect of fertiliser treatment on the fresh yield of grass grown after 21 days (daily watering; 1$^{st}$ harvest).

After 21 days, the fresh weight yields of grass (FIG. 7(a,b)) showed that all treatments, with the exception of 0.1 g AN, significantly enhanced ($p<0.05$) the growth of grass. There was no statistical difference observed between the standard polymer treatment without fertiliser and those loaded with fertiliser. The lack of benefit from use of AN fertiliser despite MG increasing yield, implies that the nitrogen in the fresh soil is not limiting, and the MG is benefiting the grass in terms of other nutrients supplied. The use of polymer containing MG failed to significantly increase the yield compared to when MG was applied alone. However, spongy PHP loaded with AN did produce a significant ($p<0.05$) yield increase compared to the application of AN alone, as the latter had failed to have an effect compared to the control.

Figure 7B:
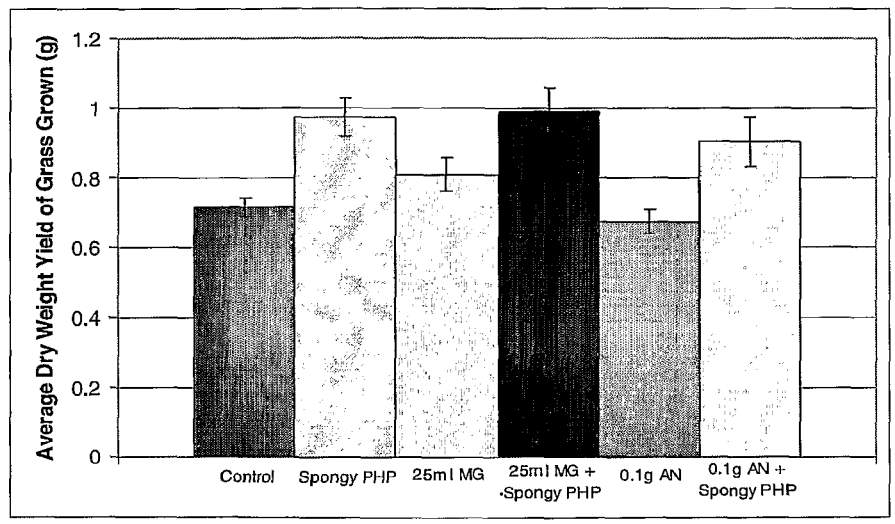
FIG. 7(b): Effect of fertiliser treatment on the dry yield of grass grown after 21 days (daily watering; 1$^{st}$ harvest).

For the dry yields of the first harvest (FIG. 7(b)), only the polymer treatments produced growth significantly different ($p<0.05$) from the control. None of the polymer treatments were significantly different from each other. Once more, spongy PHP loaded with AN did produce a significant yield increase compared to the application of AN alone.

Figure 8A:
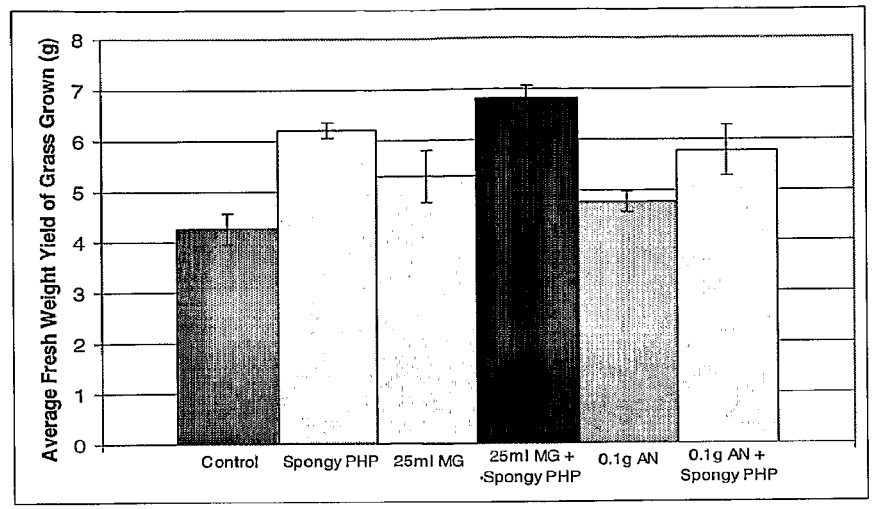
FIG. 8(a): Effect of fertiliser treatment on the fresh yield of grass grown after 42 days (daily watering; 2$^{nd}$ harvest).

For the second harvests the applications of fertiliser alone, including the use of MG, was unable to improve the fresh weight compared to the control (FIG. 8(a)). The combined treatment of 25 ml MG with spongy PHP produced the greatest mean yield (6.81 g) which was a 59.9% increase compared to the 4.26 g yield for the control. However, the combined treatment of 25 ml MG with spongy PHP did not produce a significantly different mean yield compared to the other spongy PHP based treatments.

Figure 8B:
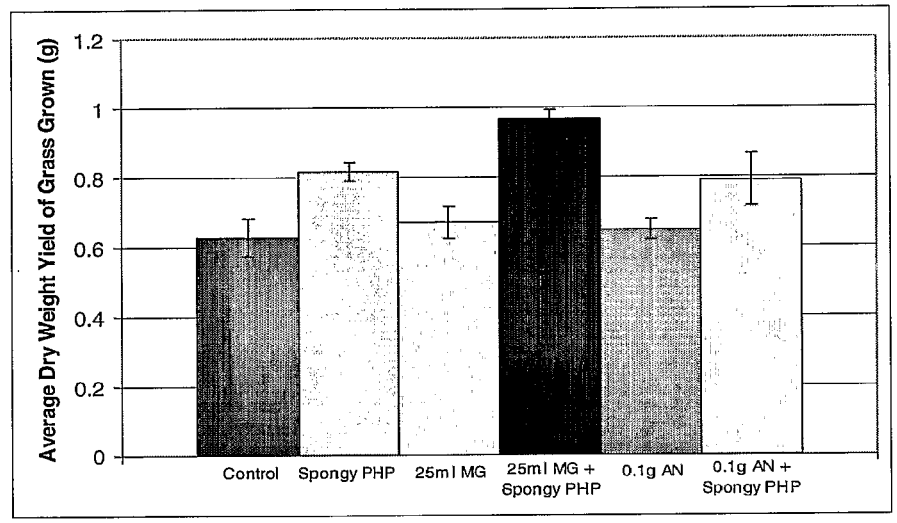
FIG. 8(b): Effect of fertiliser treatment on the dry yield of grass grown after 42 days (2$^{nd}$ harvest; daily watering).

The dry weights (FIG. 8(b)) of the second harvest followed the trend of the fresh weight, but in this case the spongy PHP containing MG had significantly higher yields than the control, 25 ml MG application and also the non-fertiliser containing spongy PHP. The mean yield achieved with the combined treatment was 0.97 g, a 54% increase on the 0.63 g mean yield obtained by the control, and a 44.8% increase on the 0.67 g average yield achieved from the direct application of 25 ml MG. This data confirms that the yield increase is not because of either the soil conditioning characteristics or the fertiliser itself, but because the spongy PHP containing MG has successfully worked as a slow release fertiliser.

Figure 9A:
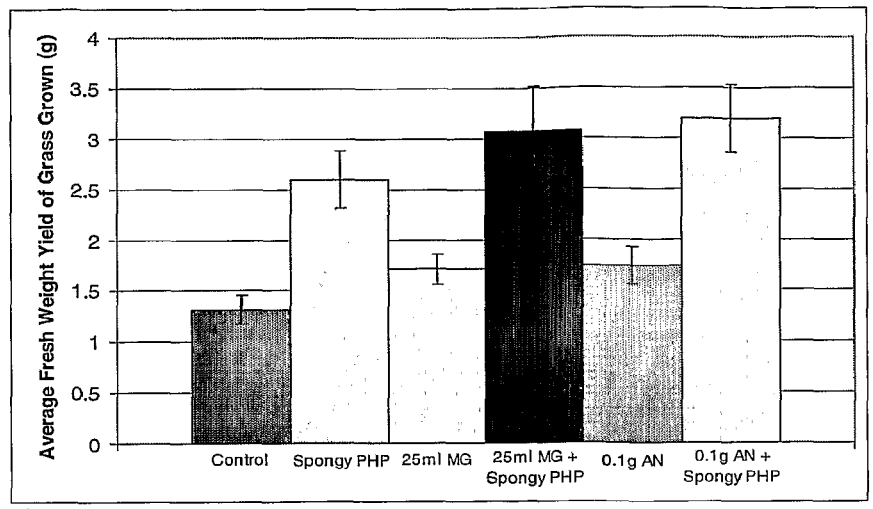
FIG. 9(a): Effect of fertiliser treatment on the fresh yield of grass grown after 63 days (3$^{rd}$ harvest; daily watering).
Figure 9B:
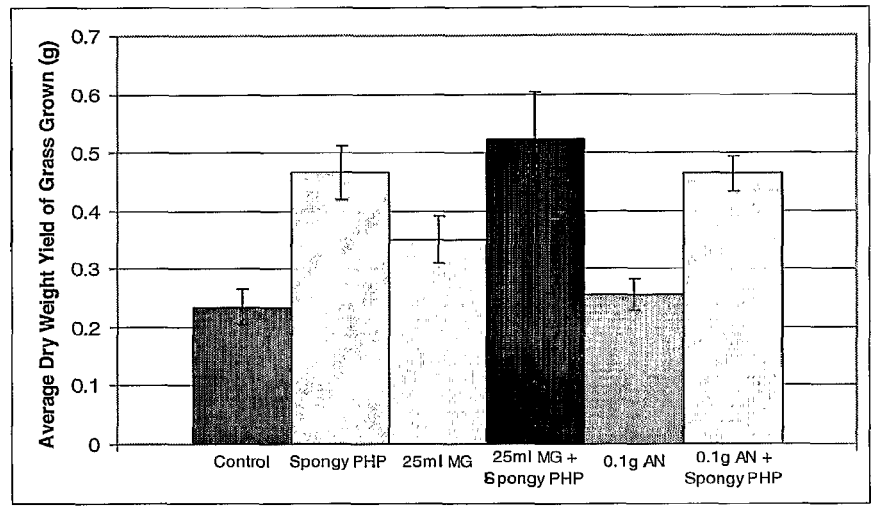
FIG. 9(b): Effect of fertiliser treatment on the fresh yield of grass grown after 63 days (3$^{rd}$ harvest; daily watering).

For the third harvest, all fresh weight yields decreased drastically and the effects of the fertiliser treatments were no longer significantly different to the control and the non-fertiliser containing spongy PHP (FIG. 9(a)). The combined MG and polymer treatment was able to increase the fresh yield from 1.71 g to 3.08 g (80.1% increase) and the dry yield from 0.35 g to 0.52 g (48.6% increase) compared to direct application of MG. As with the earlier trials with AN, it is only at the third fresh weight harvest that the 0.1 g AN began to increase yield compared to the control; however in this case, unlike earlier trials, the increase was not significantly different. The same is observed with the dry weight yields (FIG. 9(b)), with none of the fertiliser treatments significantly benefiting the yield.

TABLE 2

Rye grass growth: Average percent change with respect to the control for different polymers, fertilizers and harvests.

Significant (p < 0.05) percent change in yield with respect to the control

| Harvest | SN-PHP | | MG | | MG + SNS-PHP | | AN | | AN + SNS-PHP | |
|---|---|---|---|---|---|---|---|---|---|---|
| | Fresh | Dry | Fresh | Dry | Fresh | Dry | Fresh | Dry | Fresh | Dry |
| 1 | 46.9 | 36.4 | 21.9 | NS | 44.1 | 38.4 | NS | NS | 35.9 | 26.3 |
| 2 | 45.6 | 29.9 | NS | NS | 59.9 | 53.8 | NS | NS | 35.7 | NS |
| 3 | 98.3 | 99.1 | NS | NS | 135 | 123 | NS | NS | 143 | 98.3 |

SNS-PHP: Spongy crosslinked sulphonated-neutralized styrene PolyHIPE Polymer with 150 μm pore size;
MG: Miracle-Gro Fertilizer;
AN: Nitram Fertilizer.
Watering Regime: Daily watering;
Cubical ($5^3$ mm$^3$).
Dry = Dry yield,
Fresh = Fresh yield,
NS = No significant (p < 0.05) change in yield SSS-Polymer as Water Conservation and Slow Release Vector Grass was grown under a variety of watering conditions (daily, weekly and reduced weekly watering) and harvested after 21 days. Fresh and dry weight yields were measured and recorded for each sample. Four replications were used for each treatment.

Growth with Daily Watering

Figure 10A:
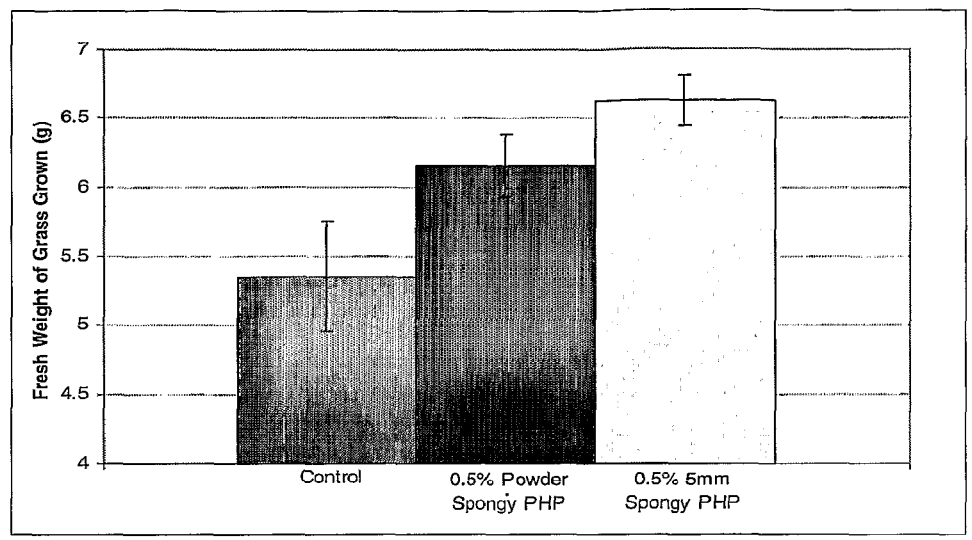
FIG. 10(a,b): Effect of spongy PHP (SNS/EHA-PHP) on grass yield after 21 day-growth (1$^{st}$ harvest) under daily watering (a) Fresh weight; (b) Dry weight.
Figure 10:
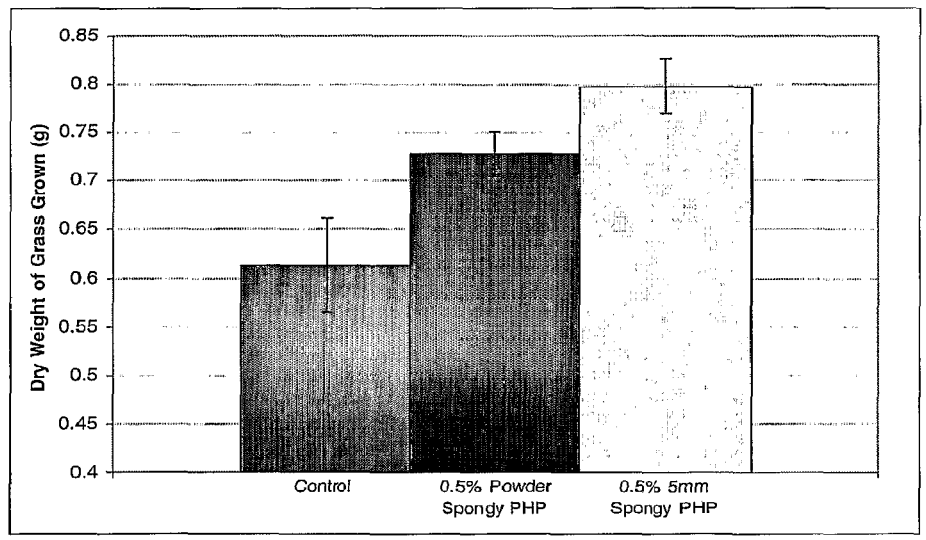

The first harvest showed that under daily watering, all of the treatments used were able to significantly increase (p<0.05) both the fresh and dry weight yields of grass compared with the control (FIGS. 10 (a,b)). The 0.5% 5 mm$^3$ spongy PHP increased the mean fresh weight by 23.9% from 5.35 g to 6.63 g when compared to the control. The same trend was observed with the mean dry weight, increasing from 0.61 g in the control to 0.80 g with the 5 mm$^3$ spongy polymer, an increase of 31.1%.

Growth Under Semi-Arid Conditions (Weekly Watering)

Figure 11A:
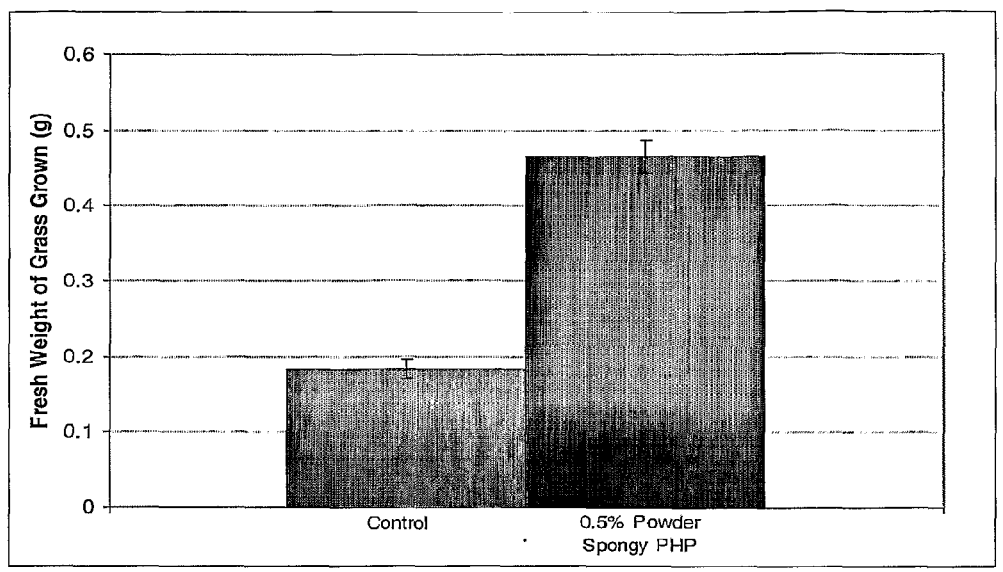
FIG. 11(a,b): Effect of spongy PHP (SNS/EHA-PHP) on grass yield after 21 day-growth (1$^{st}$ harvest) under weekly (40 ml) watering (a) Fresh weight; (b) Dry weight.
Figure 11B:
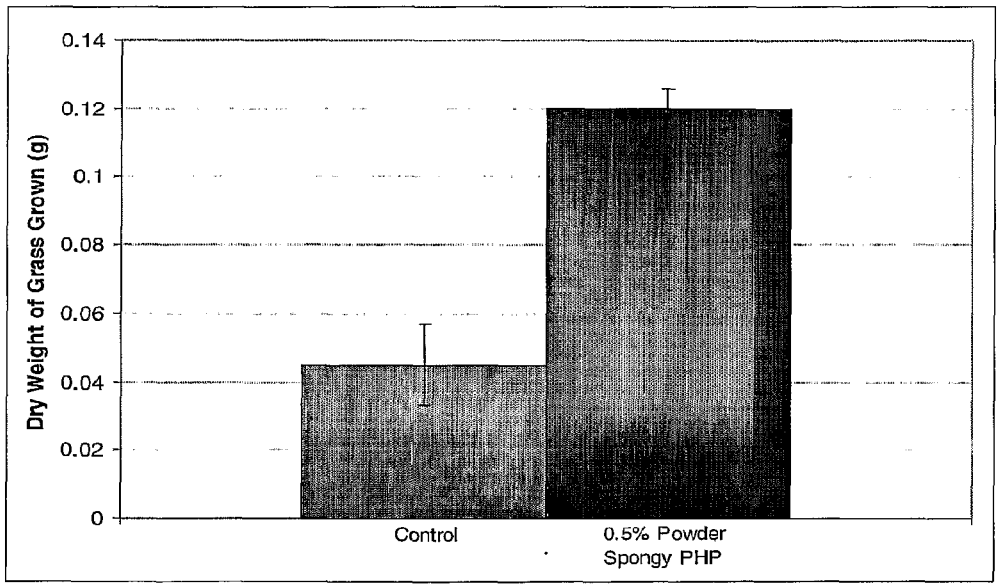

The semi-arid conditions, achieved by watering once weekly with 40 ml water, produced very low fresh and dry weights after 21 days of growth for both treatments (FIGS. 11(a,b)). However, the polymer treatment significantly (p<0.05) improved the yields recorded. The use of powdered spongy PHP more than doubled the mean fresh weight yield from 0.18 g to 0.47 g, an increase of 161%.

A similar effect was observed on the mean dry weight yield, which was increased from 0.05 g in the control to 0.12 g with the powdered spongy PHP, an increase of 140%.

Growth Under Arid Conditions (Reduced Weekly Watering)

Figure 12A:
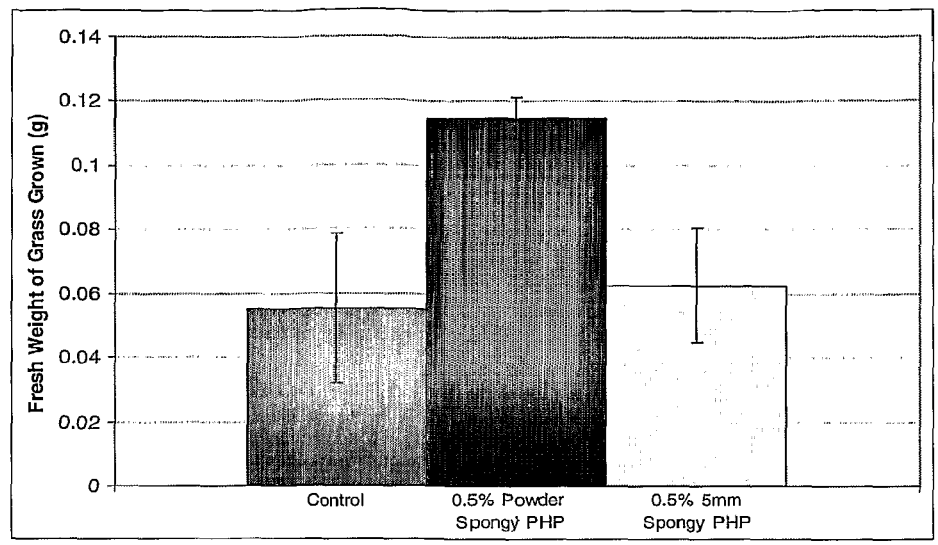
FIG. 12(a,b): Effect of spongy PHP (SNS/EHA-PHP) on grass yield after 21 day-growth (1$^{st}$ harvest) under reduced weekly (20 ml) watering (a) Fresh weight; (b) Dry weight.
Figure 12B:
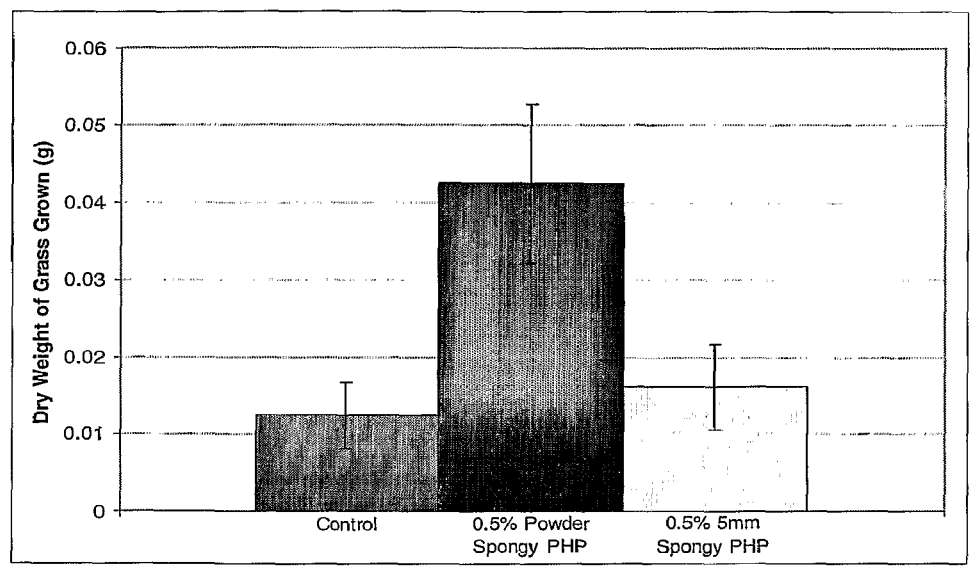
Figure 12C:
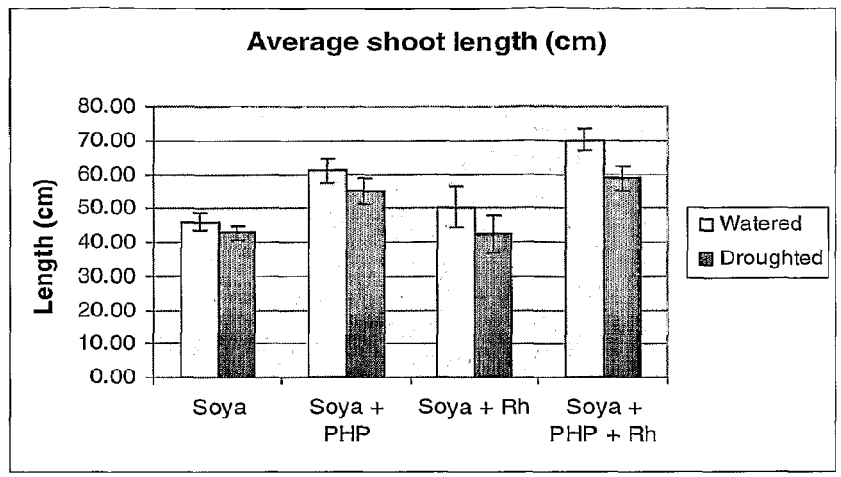
Figure 12D:
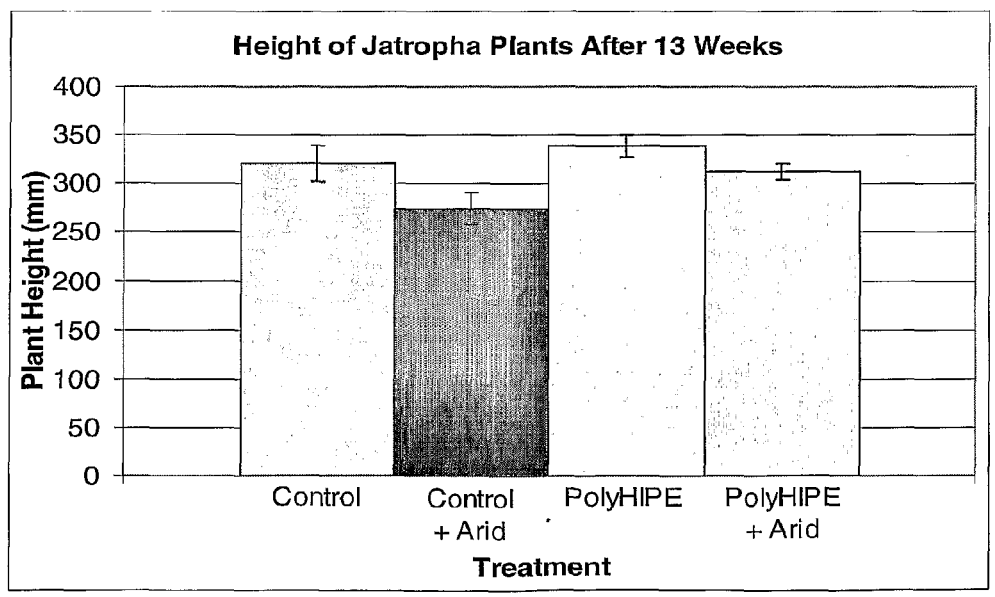
Figure 12E:
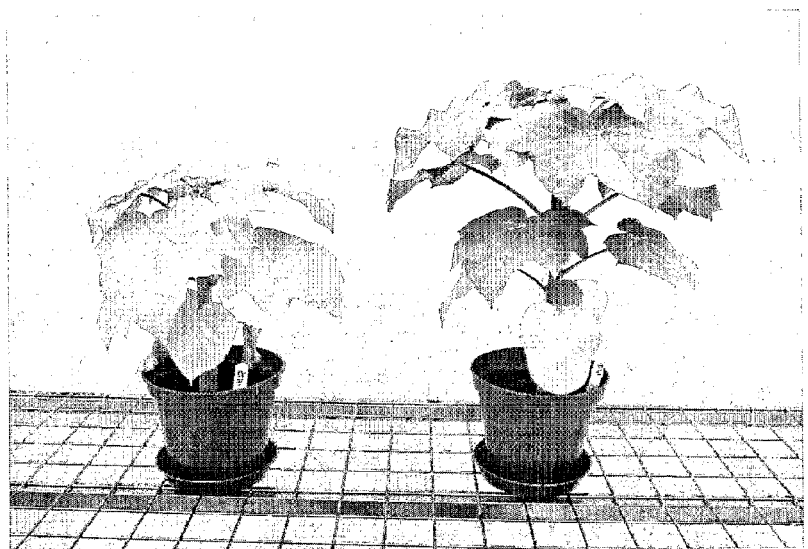
Figure 12:

For the harvest under arid conditions, only the powder spongy PHP was able to enhance the fresh and dry weight yields of the grass (FIGS. 12(a,b)). The powder version of the spongy PHP also managed to produce a statistically significant (p<0.05) increase in fresh weight to 0.12 g, an increase of 109%. The 5×5×5 mm$^3$ version of PHP had no effect on either the fresh or dry weight of the grass under arid conditions. For the dry weight yields under arid conditions, the powdered spongy PHP was able to increase the yield compared to the control. The summary of the data is given in Table 3 which indicates that especially under semi-arid and arid conditions, both powdered and particulate spongy polymers yield very good results for biomass (fresh and dry) enhancement compared with the control which contains no polymer.

TABLE 3

Rye grass growth: Average percent change with respect to the control for different polymers, fertilizers and harvests.

Significant (p < 0.05) percent change in yield with respect to the control

| | $5^3$ mm$^3$ SN-PHP (SNS-PHP) | | Powder SN-PHP (SNS-PHP) | |
|---|---|---|---|---|
| | | Dry | | Dry |
| Daily watering | 23.9% | 31.1% | 15.1% | 19.7% |
| Weekly watering | — | — | 161% | 140% |
| Reduced weekly watering | NS | NS | 109% | 242% |

SNS-PHP: Spongy crosslinked sulphonated- neutralized styrene PolyHIPE Polymer with 150 μm pore size; MG: Miracle-Gro Fertilizer; AN: Nitram Fertilizer. Variable Watering Regime. SSS polymer type: SNS-PHP powder or $5^3$ mm$^3$ particles.

The Effect of Bacteria with or without SNS-PHP on Soyabean Growth

The effect of SNS-PHP containing the bacteria (*Bradyrhizobium japonicum*) was investigated on soybean growth, again under both normal and reduced water conditions but in the presence of reduced soil nutrients. The reduction of soil nutrients is essential to show the effect of the biologically active SSS-polymers in fixing nitrogen from air since in the presence of ready soil nitrogen, legumes prefer to use the available nitrogen from soil.

Firstly the growth medium was prepared from 75% Wilkinsons' soil and 25% horticultural sand. The soil mixture was washed to remove some of the nutrients so that the effect the nitrogen fixing bacteria and nutrients in the soil on plant growth would be reduced and the effect of SNS-PHP and bacterium constructs would be evident earlier. The soil was washed in a 25% w/v ratio—i.e. 2250 g soil/9 litres of tap water in buckets. The washing was monitored by measuring the conductivity of the water over the washing period. The conductivity of tap water was 315 μS/cm. After 24 hours, with occasional stirring, the conductivity increased to 775 μS/cm. The water was changed and washed soil was added another 9 litres of tap water. After a further 24 hours the conductivity averaged 506 μS/cm. Excess water was drained and soil was then dried in trays and sterilised in an autoclave in 500 g aliquots in autoclavable plastic bags. The nitrogen, phosphorus & potassium content of the soil were measured, in triplicate, before and after washing.

|  | Before washing | After washing |
|---|---|---|
| Nitrogen | 0.22 w % | 0.14 w % |
| Phosphorus | 8.66 µg/ml | 5.87 µg/ml |
| Potassium | 203 µg/ml | 108.5 µg/ml |

Preparation of *Bradyrhizobium japonicum* Broth

*Bradyrhizobium japonicum* was streaked for single colonies on a plate containing nitrogen free nutrient solution. This was repeated on a second plate to ensure pure single colonies. A single colony was then inoculated into sterile nitrogen free nutrient solution to use as a starter culture and incubated in a shaker at 160 rpm for 72 hours at 26° C. 1 ml of starter culture was then inoculated into 500 ml flasks containing 170 ml of nitrogen free nutrient solution and incubated in a shaker at 160 rpm for 72 hours at 26° C.

The nitrogen free nutrient solution was made up of 200 ml Hoaglands nitrogen free nutrient solution, 0.2 g sodium carbonate, 10 g mannitol, 1 g yeast and 800 ml deionised water. For nitrogen free agar medium, 7.5 g agar was added per litre of nutrient solution.

Planting

Soybeans (variety PAN) were grown in 13 cm diameter pots in triplicate using 8 different treatments:

1. Control—no polymer or *rhizobium*
2. +(SNS-PHP) polymer
3. +*rhizobium*
4. +polymer+*rhizobium*
5. Droughted—no polymer or *rhizobium*
6. Droughted+(SNS-PHP) polymer
7. Droughted+*rhizobium*
8. Droughted+(SNS-PHP) polymer+*rhizobium*

500 g of soil (already washed with water to remove excess nutrients) mixture was added to each pot. One soybean seed was planted in each pot and covered with 1" of soil mixture. Sulphonated polymer (SNS-PHP) was added at the rate of 0.5% w/w—i.e. 2.5 g/pot in the soil below the seed. 60 ml of *rhizobium* broth was added to the surface of pots with only broth added. For pots with both polymer and *rhizobium*, 2.5 g polymer was soaked in 60 ml of broth for 3 days. The soaked polymer was mixed with the soil and the excess broth was poured over the surface after planting. Normally watered plants were given 100 ml water per pot twice a week. Droughted plants were given 50 ml water per pot twice a week. Plants were watered in the top of the pot to simulate more natural watering conditions.

Results

After 8 weeks growth the length of the shoots were measured. The results are shown below, and illustrated in the graph of FIG. 12c.

TABLE 4

The effect of SNS-PHP in the absence or presence of nitrogen fixing bacteria on the biomass yield under normal (200 ml/week) and drought (100 ml water/week) conditions.

| Type of treatment | Average shoot length (cm) Normal watering (200 ml/week) | Average shoot length (cm) Droughted (100 ml/week) |
|---|---|---|
| Control (soya only) | 46.0 | 42.7 |
| Control + SNS-PHP | 61.0 | 55.0 |
| Control + Rhizobium | 50.3 | 42.3 |
| Control + Rhizobium + SNS-PHP | 70.0 | 58.7 |

SSS-polymer type: SNS-PHP $5^3$ mm$^3$ form.

Plants with only *rhizobium* added did not produce a significant increase compared to the control, but plants with only polymer added did produce an increase both for normally watered (32.6%) and droughted (28.9%). A bigger increase was observed for plants with polymer soaked with *rhizobium* 52.2% for normally watered plants and 37.5% for droughted plants compared to the control. The actual biomass increases are even more compared with the increases in height only.

Still further trials were carried on Jatropha plants in normal watering conditions (400 ml water per pot twice weekly administration with 200 ml each time) and also under arid conditions (200 ml water per pot twice weekly administration with 100 ml each time). Each pot has 500 g soil mixture (Wilkinsons' Multi-Purpose Compost with horticultural sand) and 2.5 g SNS-PHP (i.e., 0.05 w %). The pots were fertilised every 8 weeks with Miracle-Gro All Purpose Concentrated Liquid Plant Food. Fertiliser is diluted for application. Recommended dose is 5.5 ml per litre of water and given every 7-10 days. Jatropha is given 50 ml of dilute fertiliser at a concentration of 11 ml per litre (i.e. double concentration) but only once every 8 weeks.

Figure 12G:
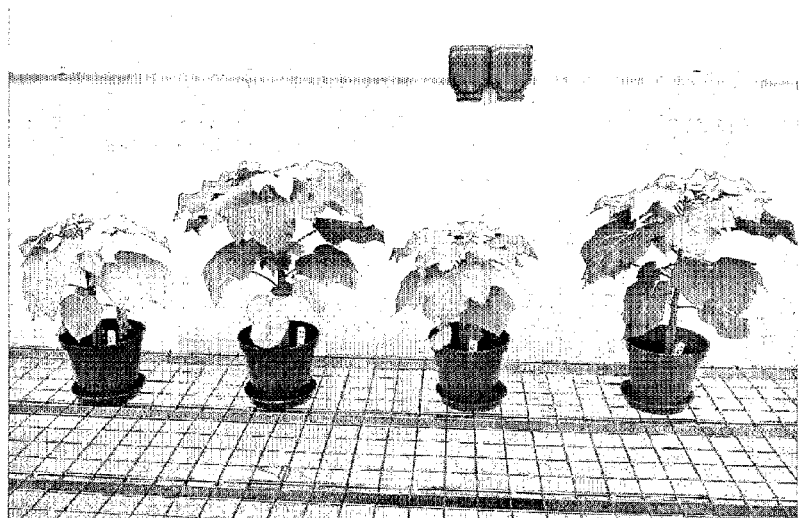

The results after 24 weeks are illustrated graphically in FIG. 12d. Photographs of the plants in the trial after 18 weeks are shown in FIGS. 12e-g. Again the improvement brought about through the presence of the PHP is clear.

Pea Crop Yields with *Rhizobium* Inoculant

A set of trials were conducted to compare the effects of both the soil conditioner and the bacterial broth on the yields of pea plants. The yields of the pea pods were measured separately to the rest of the shoot biomass (stems and leaves), to allow for a comparison between crop yields as well as the total (i.e. stem and pods) biomass yields.

Total Yields of Pea Pod Crop

Figure 13A:
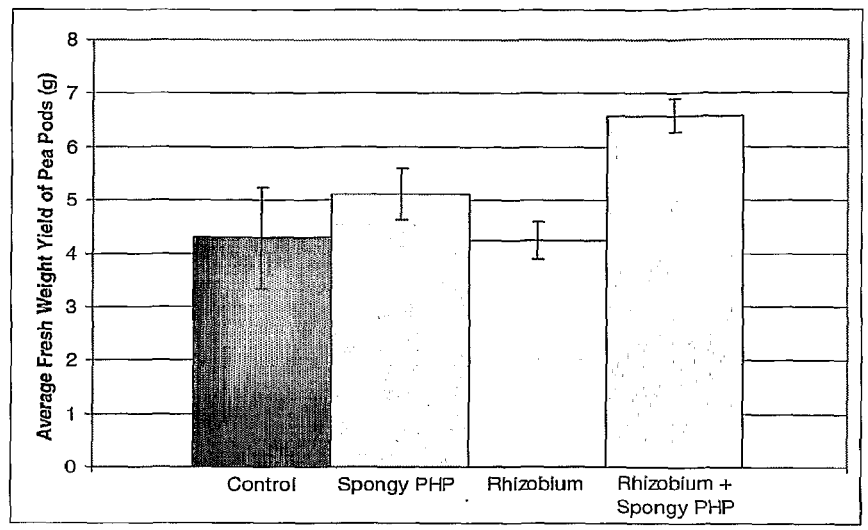
FIG. 13(a,b): Effect of inoculation treatment on the yield of pea pods after 41 days with or without spongy SNS-PHP. (a) Fresh weight, (b) Dry weight.
Figure 13B:
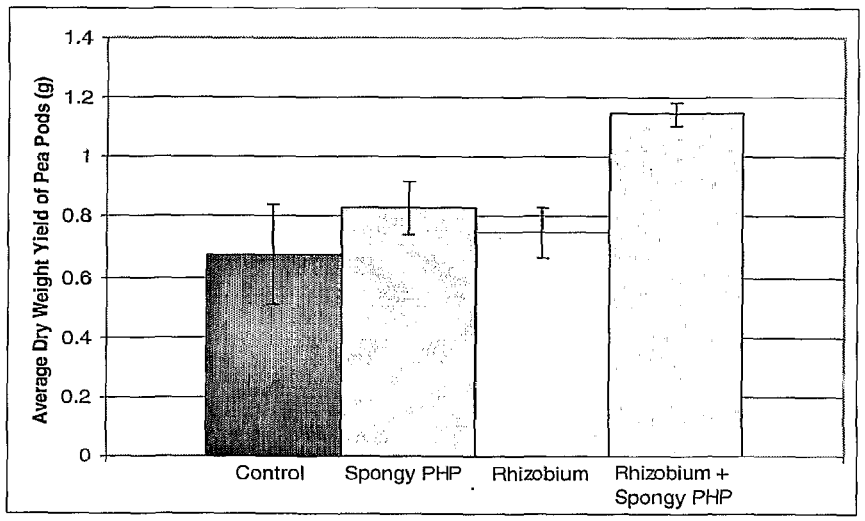

Because of the large variation observed in the control yields, the two sample t-tests of independence assuming equal variance at 95% confidence showed that none of the treatments were actually able to significantly increase the fresh yield compared to the control (FIG. 13 (*a*)). However, the mean yield of the combined *Rhizobium* and spongy PHP treatment was significantly different to the applications of just *Rhizobium leguminosanan* (55.2% increase from 4.24 g) and just spongy polymer (28.8% increase from 5.11 g).

For the dry weight yields of the pea crop (FIG. 13(*b*)), the combined *Rhizobium* and polymer treatment was able to significantly enhance the yields compared to all treatments, including the control. The combined treatment actually increased the average yield to 1.15 g compared to 0.68 g for the control (69.1% increase) and 0.75 g compared to the direct application of *Rhizobium* (52.7% increase). Therefore, despite the large variation in control fresh weight yields, the data for the dry weight yields does confirm that the combined treatment is most beneficial to the growth of pea pods.

Although the combined *Rhizobium* and polymer treatment does significantly increase dry yield, the use of broth inoculant alone has had no effect on either the fresh or dry weight yields. This indicates that when applied directly to the soil, the bacterial broth is an unsuitable inoculant. Reasons for this may be that the concentration of the bacteria within the broth is not high enough to efficiently colonise the soil to ensure contact with the roots. It is also possible that the bacteria are unable to attach to soil particles when within a broth, and hence get washed away upon watering. The use of spongy PHP has overcome these problems by acting as a support matrix to encourage the growth of *R. leguminosarum*. The polymer not only provides a moisture store within the soil, but also acts as a support matrix for the bacteria, allowing them to grow in a more stable environment as well as encouraging interaction with plant root systems.

Pea Shoot Biomass Yields

Figure 14A:
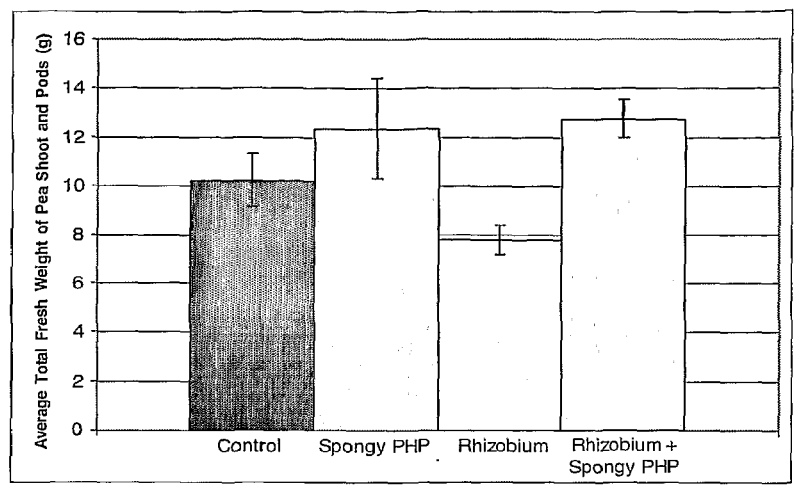
FIG. 14(a,b): Effect of inoculation treatment on the shoot biomass yield of pea plants after 41 days with or without spongy SNS-PHP.

The shoot biomass yields (i.e. shoot and peas) were also measured and recorded. The fresh weight yields (FIG. 14(a)) again showed that there were no significant differences in yield between the control and each of the other treatments. However, the combined *Rhizobium* and polymer treatment did result in a significantly different yield increase from 7.77 g to 12.77 g (64.4% increase) compared to the plain *Rhizobium* treatment.

Figure 14B:
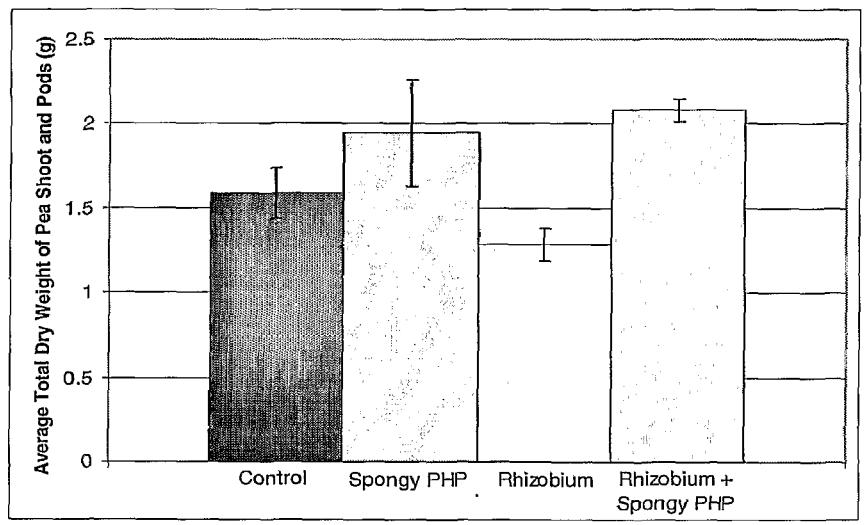

For the dry weight yields (FIG. 14(b)), one treatment did produce a significantly different yield to the control, and that was the combined *Rhizobium* and polymer treatment. The combined treatment again resulted in a significantly different yield increase from 1.29 g to 2.08 g (61.2% increase) compared to the plain *Rhizobium* treatment. However, unlike the yields for the pea pods, the combined treatment was not significantly different to that observed with just polymer was applied, therefore it is not certain whether this difference is due to the polymer association with bacteria or the soil conditioning properties. It is also possible that the PolyHIPE Polymer+*Rhizobium* constructs when associated with the root system enhance crop yield at the expense of overall biomass.

The summary of the results is shown in Table 5. As seen from this table, the only significant yield enhancement is achieved when sulphonated—neutralized spongy PHP (SNS-PHP) is used as SSS with *rhizobium*. This is because enhancement of bacterial infection and nodulation since the water and nutrient stress is not present. As shown in the next section, root association results in nodulation.

TABLE 5

The effect of SSS Polymer (Sulphonated, neutralized spongy polymer, SN-PHP) + Rhizobium constructs on average crop and total biomass when using sulphonated-neutralized spongy PHP (SNS-PHP) showing the percentage changes in the fresh (F) and dry (D) yield.

| | Significant (p < 0.05) percent change in yield with respect to the control | | | | | |
|---|---|---|---|---|---|---|
| Yield | SNS-PHP (No Rhizobium) | | Control + Rhizobium | | SNS-PHP + Rhizobium | |
| Type | Fresh (F) | Dry (D) | Fresh (F) | Dry (D) | Fresh (F) | Dry (D) |
| | NS | NS | NS | NS | NS | 69.6 |
| Total | NS | NS | NS | NS | NS | 31.0 |

Figure 15A:
FIG. 15(a,b,c): *Rhizobium leguminosarum* inoculated spongy PHP (SNS-PHP) before being used in the cultivation of pea at different magnifications.
Figure 15B:
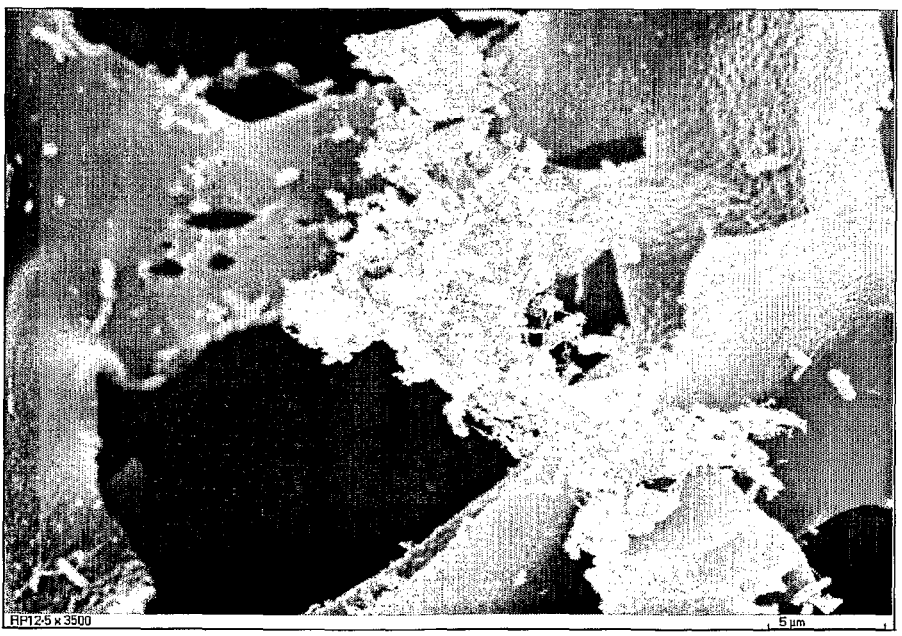
Figure 15C:
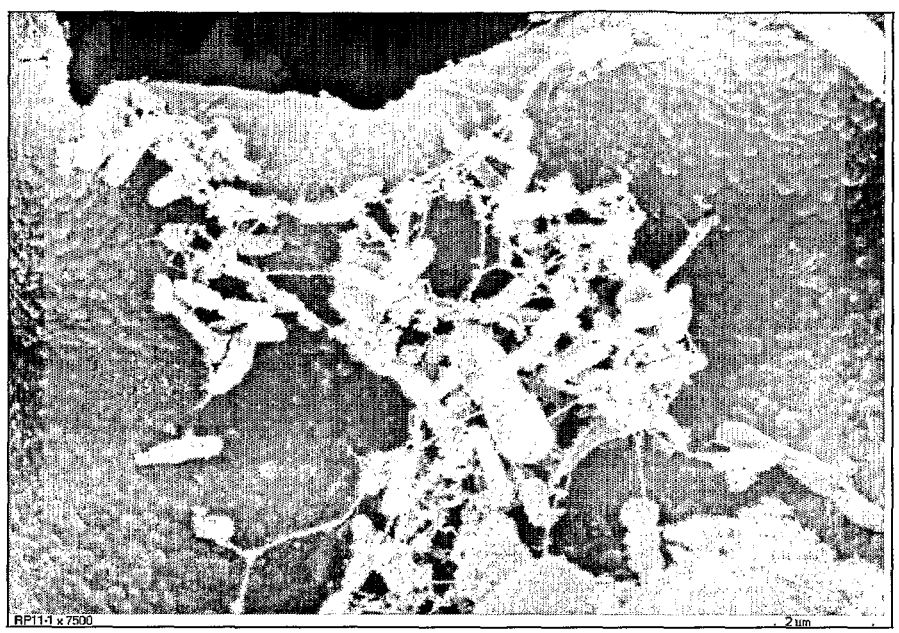

Dry = Dry yield,
Fresh = Fresh yield,
NS = No significant (p < 0.05) change in yield Bacterial and Root Associations with SNS-PolyHIPE Polymer To determine if *R. leguminosarum* is capable of growing within the pores of PolyHIPE, the bacterial broth was soaked into the pores of autoclaved samples of PolyHIPE and then washed and fixed for examination under SEM. Cross section analysis of the samples (FIGS. 15(a,b,c)) shows the presence of extra-cellular matrix from bacteria and microscopic debris from the inoculant's broth surrounding colonies of bacteria that grow extensively throughout the polymer structure after just 7 days incubation. In the soil, the polymer provides a relatively stress free environment compared to the soil alone, and allows the bacteria to thrive and avoid being displaced by water movement.

Figure 16:
FIG. 16(a,b,c,d) Association of pea root with sulphonated—neutralized spongy PHP (SNS-PHP).
Figure 16B:
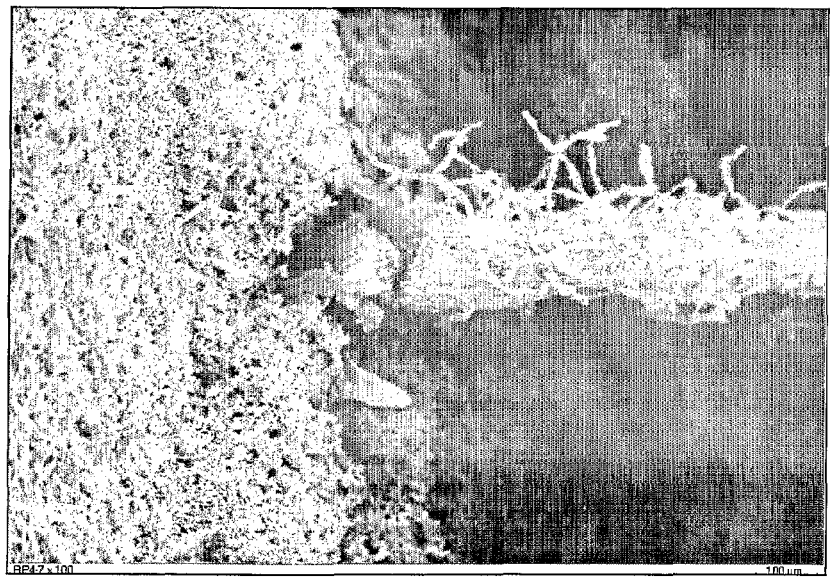
Figure 16C:
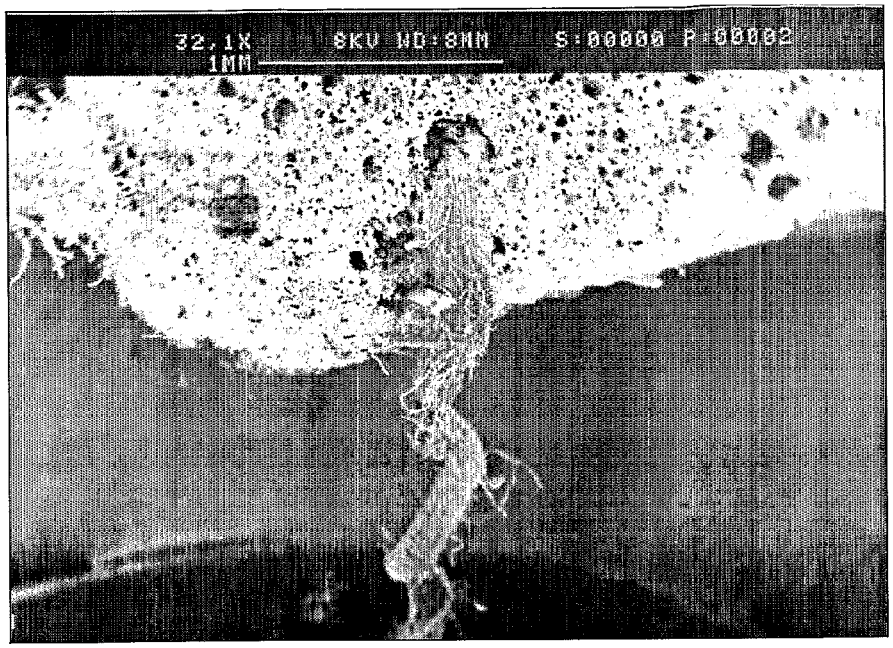
Figure 16D:
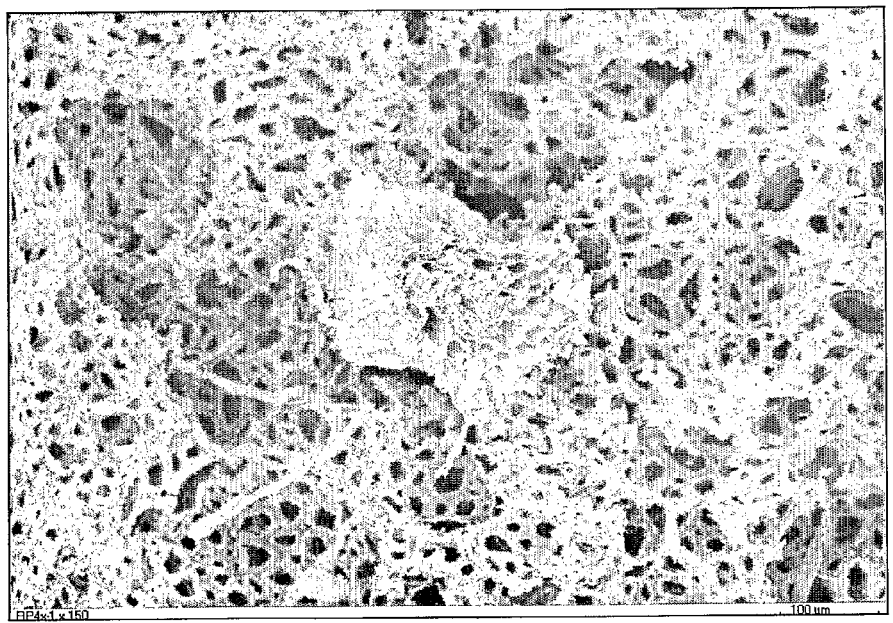
Figure 17:
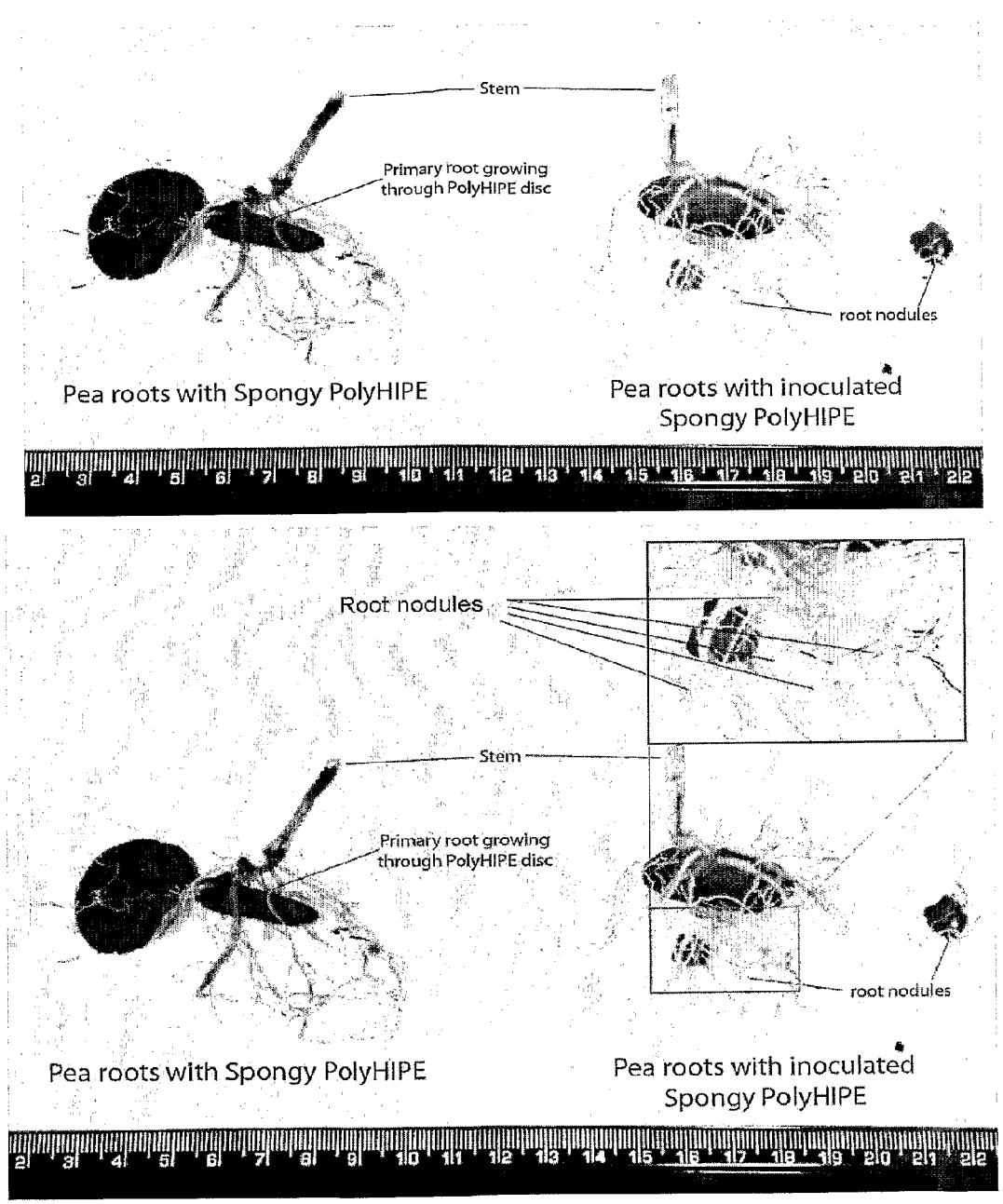
FIG. 17(a) Photographs of pea plant roots associated with spongy PHP (used just under the seed in the form of a disk) showing that the roots after passing through the SSS-polymer (SNS-PHP) are nodulated whereas those without contact with the SSS-Polymer are not nodulated.
FIG. 17(b): SEM of the pea root nodule formed after being infected with the bacteria within the spongy PHP (SNS-PHP).
FIG. 17(c): SEM of pea root within the spongy polymer (SNS-PHP) showing the presence of debris and PHP structure.
FIG. 17(d): Pea root growing through the spongy PHP (SNS-PHP) and creating debris
FIG. 17(e): Distortion of the PHP structure and interconnects due to the root growth and the presence of filamentous structures.
FIG. 17(f): Creation of a microenvironment containing roots, bacteria and spongy PHP (SNS-PHP).
FIG. 17(g): Bacterial colony in the spongy PHP (SNS-PHP) during the growth of pea.
FIG. 17(h): Bacteria growing on the root surface after being picked up from the spongy PHP (SNS-PHP).
FIG. 17(i): Detail of fibrous structures formed on the surface of *Rhizobium* inoculated using spongy PHP (SNS-PHP) during Pea cultivation (Magnification x5000).
Figure 17:
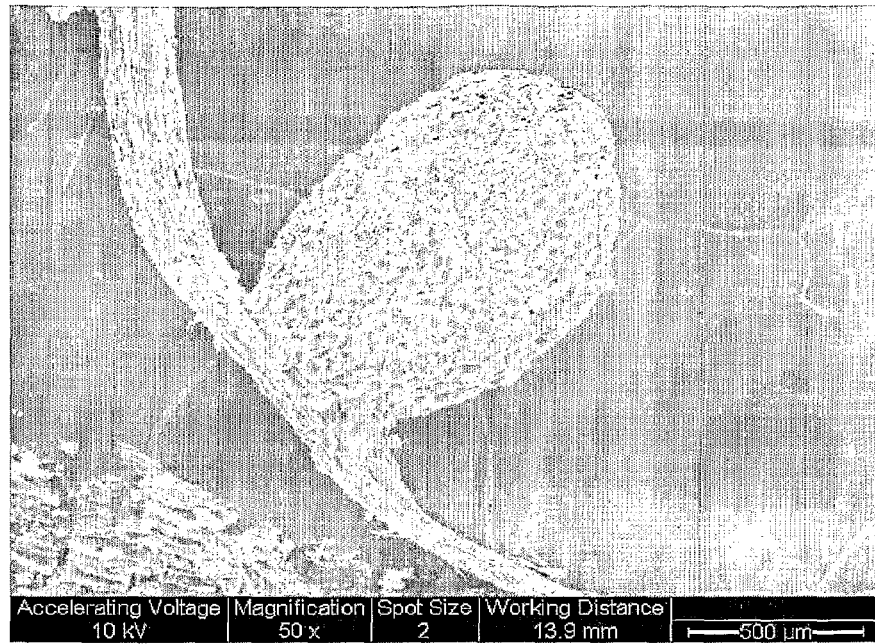
Figure 17:
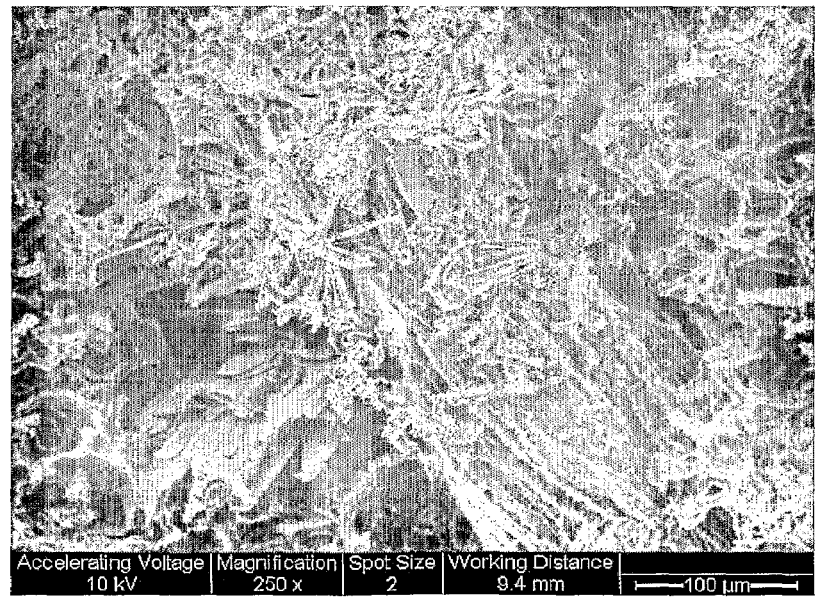
Figure 17:
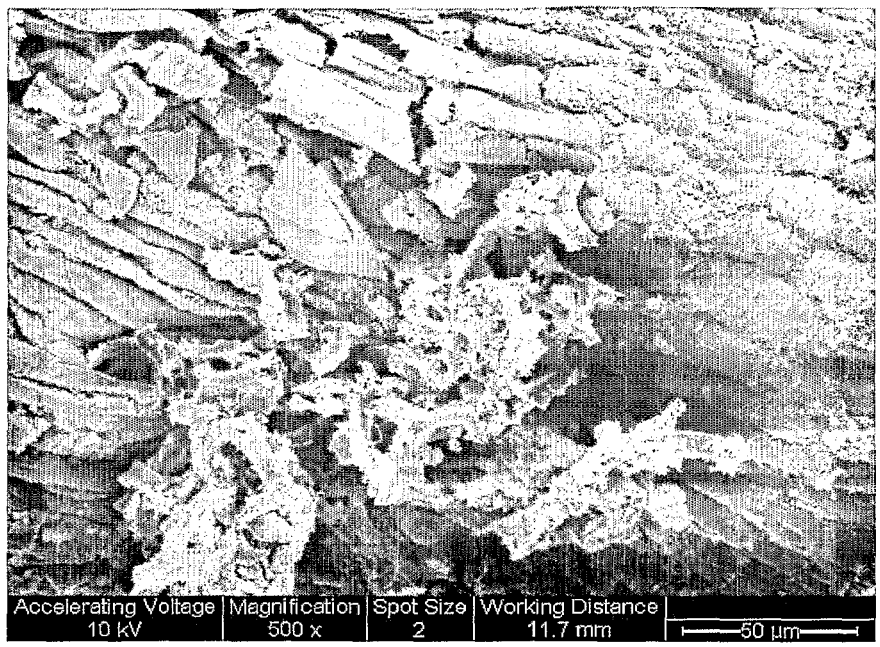
Figure 17:
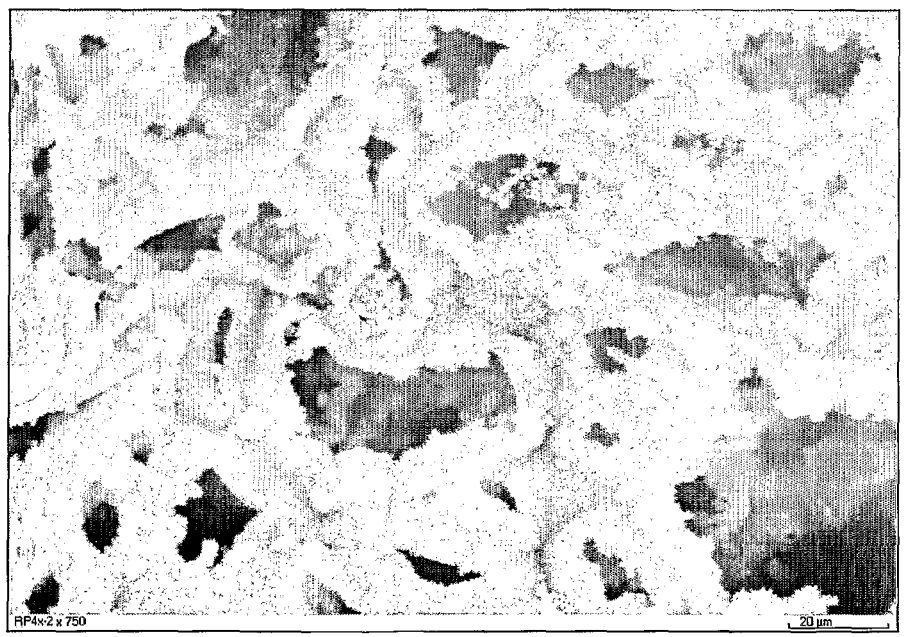
Figure 17:
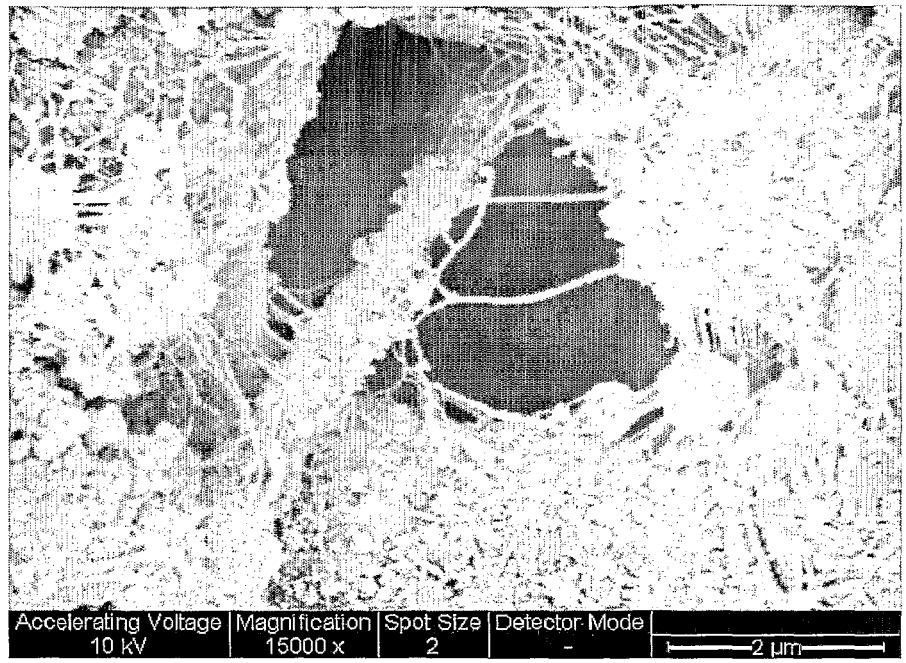
Figure 17:
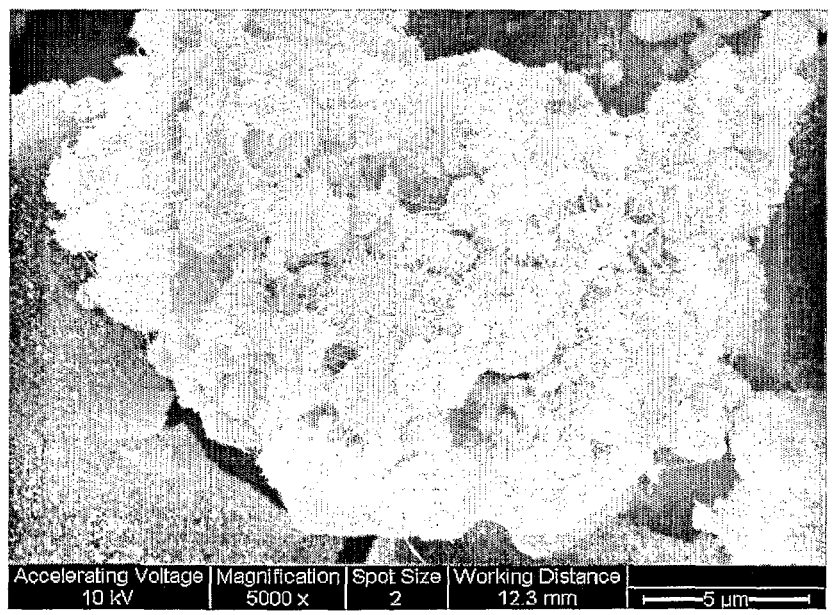
Figure 17:
Figure 17I:
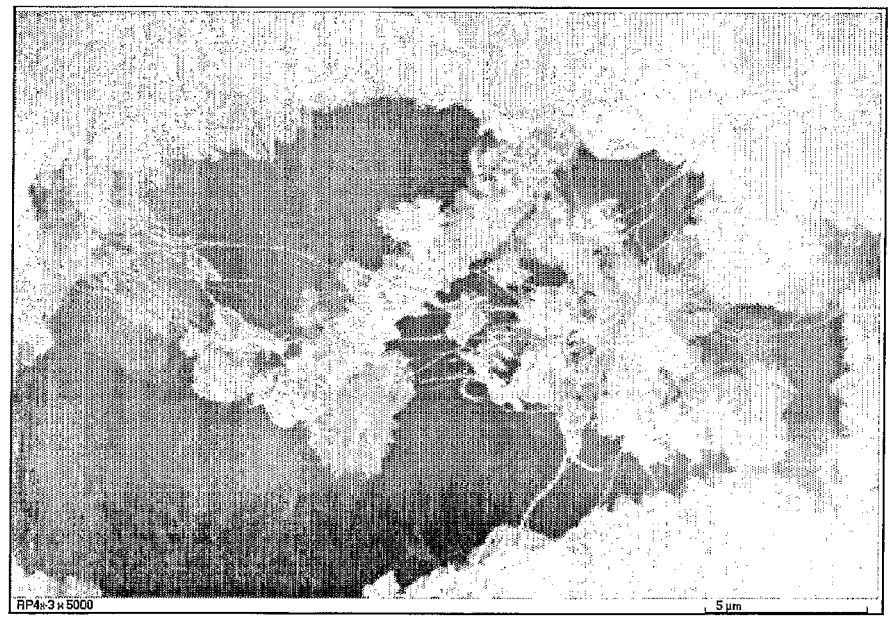

The PolyHIPE structure also attracts the roots as they move through the soil. The roots actually penetrate through the structure of the SNS-PolyHIPE Polymer, which becomes entwined within the entire root system of the pea plant (FIGS. 16 (a,b,c,d)). This phenomenon was also observed when using the SNS-PolyHIPE Polymer as a soil conditioner for growing grass. When the polymers have been prepared with the bacterial broth, the bacteria are able to grow within the porous matrix whilst the seed germinates. As the roots reach and penetrate through the polymer structure, they come into contact with large numbers of bacteria within confined environment which enhances bacterial/root association leading to root nodule formation and the production of root exudates (FIGS. 17 a,b,c,d,e,f,g,h,i). It is this rapport that allows SNS-PolyHIPE Polymer to enhance the symbiotic relationship between *Rhizobium* and pea plants, and hence increase inoculant use efficiency and improve yield.

During the cultivation of the pea crop using *Rhizobium* within the SNS-PolyHIPE Polymer, it was observed that the SNS-PHP structure is coated with root exudates as seen in FIG. 17(e,i).

Figure 18:
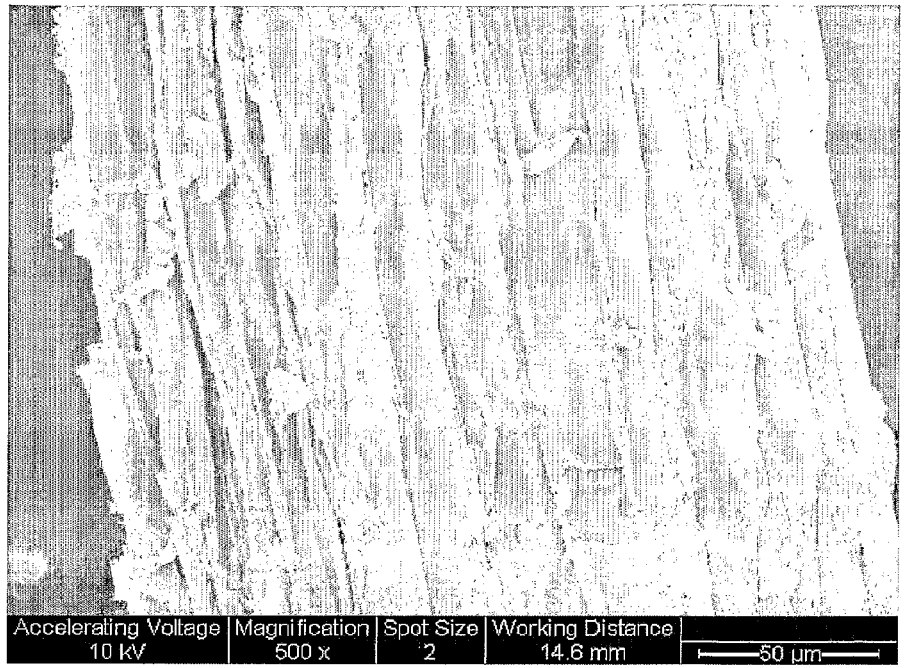
FIG. 18(a): Fibrous root structure after passing through the spongy PHP (SNS-PHP).
FIG. 18(b). Fibrous root structure when the root is solely grown in soil.
Figure 18:
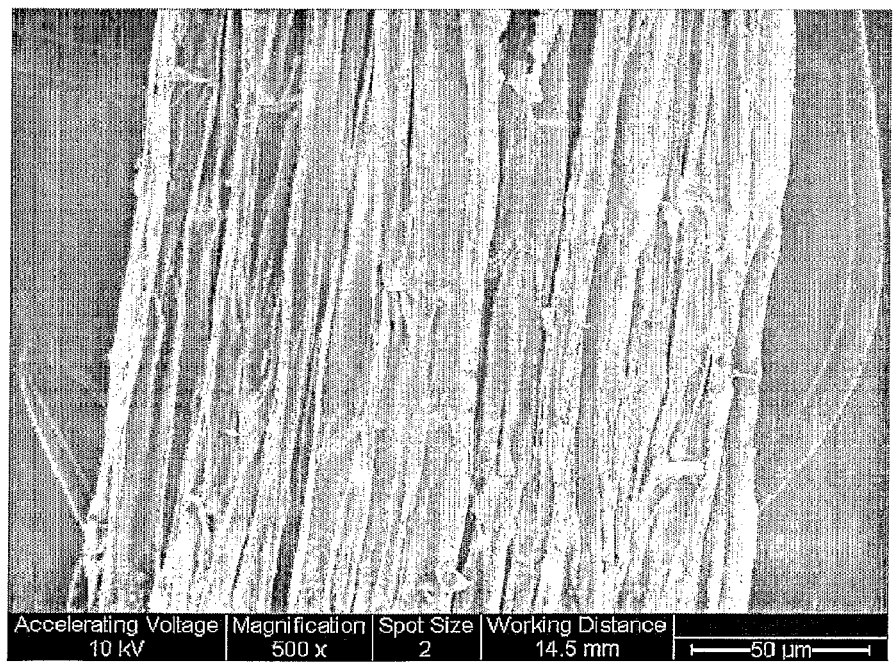

It was also observed that the pea roots which grow through the SSS-media (SNS-PHP) have more rugged structure (FIG. 18(a)) compared with the roots which grow without any interaction with the SSS-media as seen in FIG. 18(b).

Tissue Analysis of Pea Crop and Shoots

As shown in Table 6, the use of SSS-Polymer with or without being inoculated with *Rhizobium* also increases the nitrogen and phosphorous content of the pea crop compared with the control (no polymer or no additional bacteria). This increase is also marked when the equivalent amount of bacteria is placed in the soil instead of within the spongy polymer. Since nitrogen and phosphorus are the important components of the proteins, it also implies that the protein content of the pea crop is also enhanced when polymers are used.

Similarly, it is observed that the metal content of the pea as well as that of the shoots in most cases are also enhanced compared with the control. These enhancements are due to the fact that the spongy polymer acts as an ion exchange media and positively charged ions are adsorbed by the polymer and subsequently taken up by the plant.

TABLE 6

Percent difference in nutrient/metal content compared to the control (Soil contains no SSS-polymer, no additional rhizobium).

|  | Spongy Shoot | Spongy Pea | Bacterial Shoot | Bacterial Pea | Inoculated Shoot | Inoculated Pea |
|---|---|---|---|---|---|---|
| Nitrogen | 9.63% | 20.11% | −45.85% | 7.06% | −11.59% | 65.49% |
| Phosphorus | 15.01% | 16.96% | −41.07% | 28.85% | 5.61% | 90.18% |
| Potassium | 21.87% | 11.80% | −36.44% | 19.93% | 15.84% | 81.15% |
| Magnesium | 26.63% | 22.67% | −20.16% | 10.81% | 25.53% | 78.11% |
| Calcium | 14.37% | 24.55% | −21.12% | 9.11% | 26.95% | 88.72% |
| Sulphur | −17.36% | 9.75% | 13.51% | 28.31% | 13.19% | 70.37% |
| Manganese | 44.01% | 15.85% | −20.58% | 4.66% | −10.95% | 7.74% |
| Copper | 35.93% | −10.83% | −33.11% | 17.95% | 10.71% | 25.87% |
| Iron | 156.23% | 81.44% | 403.78% | 106.05% | 34.35% | 54.03% |

Intercropping of Legumes and Non-Legumes

In order to promote nitrogen fixation through bacteria and plant association and share nitrogen with another plant, we use pea (legume) and grass (non-legume). Other useful examples of intercropping to enhance nitrogen transfer include perennial plants such as Scotch Broom or clover (legumes) and jatropha (non-legume) for biomass production as energy crops without nitrogen fertilizers under water-nutrient stress. There are several tree species which are capable of fixing nitrogen (Nitrogen Fixing Trees, NFTs) which are particularly important agroforestry in arid/semiarid marginal land. They include, for example, desert ironwood (*Olneya tesota*), paloverde (*Cercidium microphyllum*), mesquites (*Prosopis velutina, Prosopis glandulosa*), acacia species (*Acacia koa, Acacia confusa*, etc.), Haole (*Leucaena leucocephala*), etc. Some of these nitrogen fixing trees are also considered as weeds and they can be planted with energy crops such as willow, poplar, jatropha etc. so that there is no competition with the food chain. The transfer of nitrogen from legumes to non-legumes will be further enhanced when the roots from both crops go through the SSS-media as a suitable environment for sharing nitrogen.

Figure 19:
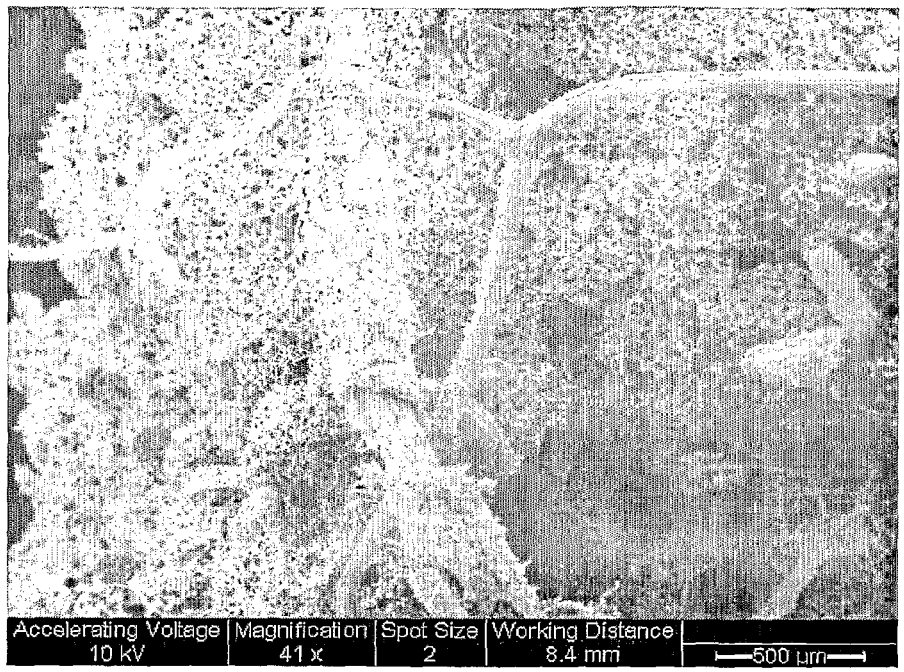
FIG. 19(a,b,c,d): Grass and pea root association with the spongy PHP (no inoculation) showing the presence of two different types of roots going through the SSS-polymer (SNS-PHP) at different locations and magnifications.
Figure 19:
Figure 19:
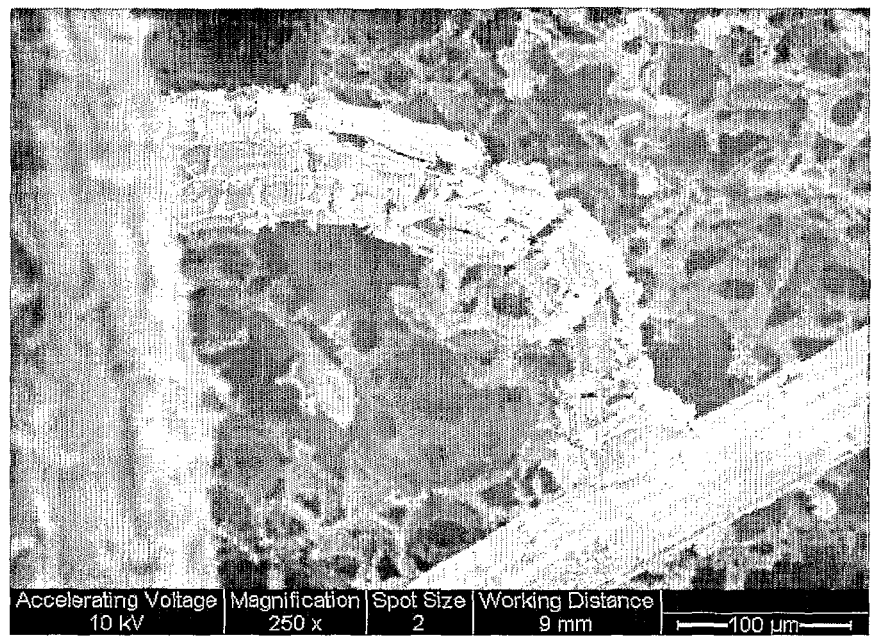
Figure 19:
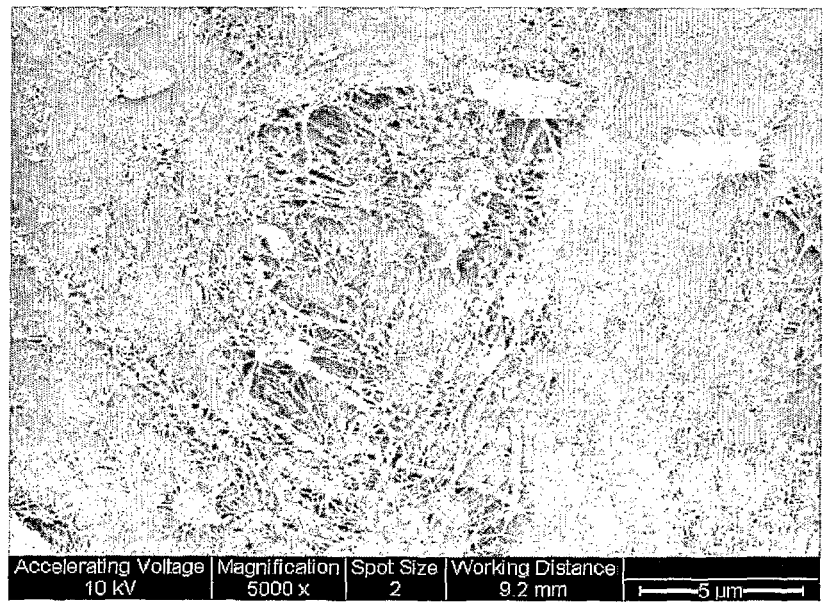
Figure 20:
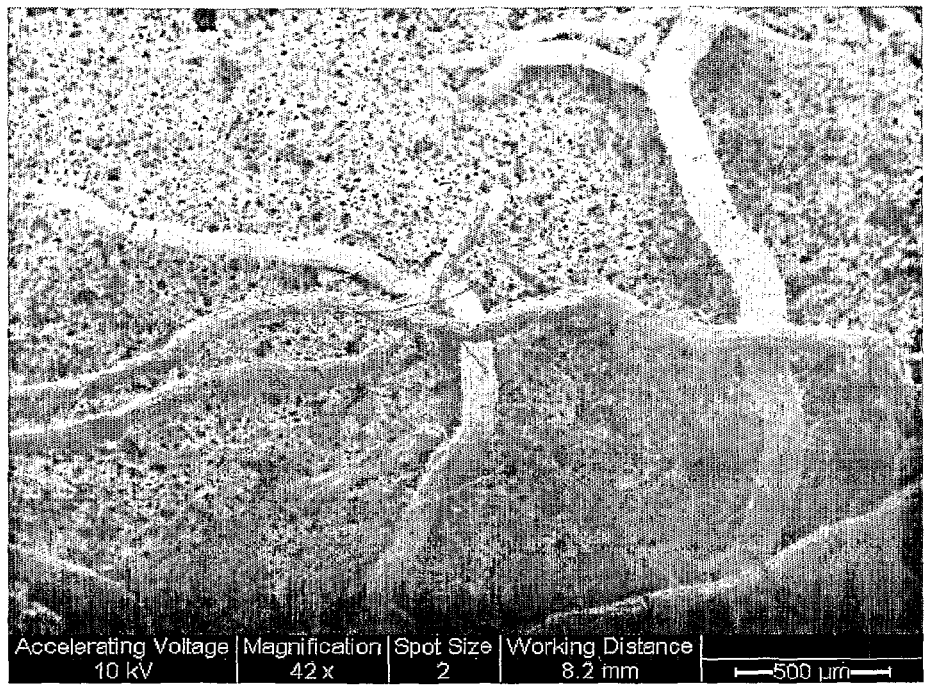
FIG. 20(a,b,c): Grass and pea root association with the spongy PHP (SNS-PHP) inoculated with *Rhizobium* showing the presence of bacteria and fibrous structures.
Figure 20:
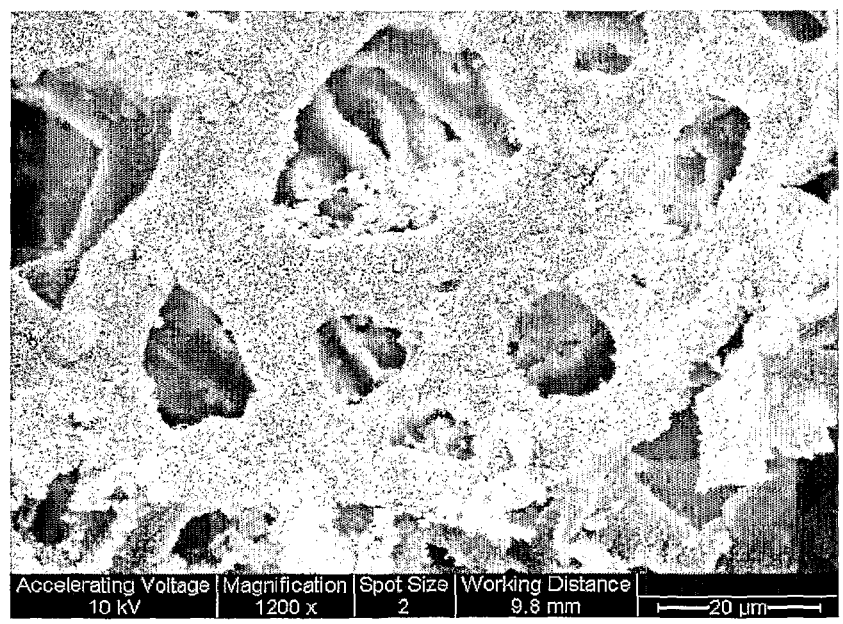

Inter-cropping in the presence of SSS-media was investigated in order to observe the root-root interactions within the symbiotic-media. In these experiments, each plant pot was planted with grass seeds and a single pea seed. Soil was treated with 0.5 g liquid fertilizer (Miracle Gro) before the addition of 0.5 wt % spongy PHP in the form $5^3$ mm$^3$ cubical SNS-PHP particles which were inoculated with bacterial broth. At the end of the 42 days of cultivation with daily watering, SNS-PHP particles were recovered and examined under SEM. Two types of SNS-PHP were used. In the first instance, we used SNS-PHP without any *Rhizobium*. FIG. 19(*a,b,c,d*) illustrates the presence of two different types of root growth through the SNS-PHP and the detail of the micro-environment. When the SNS-PHP contains *Rhizobium* roots of the two plants (grass and pea) also present within the SNS-PHP but the micro-environment of SNS-PHP now contains root exudates as shown in FIG. 20(*b,c*), similar to the micro-environment created when only pea plant was present as shown in FIG. 17(*e,i*).

Mixed Bacteria Inoculation

Beneficial soil fungi play large role in nitrogen and phosphorous utilization in most plants. They also help in water uptake and inhibition of root pathogens. Similar to the delivery of nitrogen fixing bacteria, Rhizobia, to the plant roots, sulphonated, neutralized spongy PolyHIPE Polymer (SNS-PHP) was used as the delivery system for beneficial soil fungi. Myconhizal fungi were supplied by PlantWorks Limited, Kent, Sittingboume, UK under the trade name Rootgrow. 5 g of Rootgrow was mixed into 45 ml Hoaglands nitrogen free nutrient solution and then poured over sulphonated neutralised PolyHIPE Polymer discs in a Petri dish. The dishes were then covered in foil to block out the light and left in the growth cabinet at 28° C. for 14 days. After 14 days, the samples were washed in PBS and Glutardialdehyde then dehydrated in ethanol before being critically point dried for SEM analysis.

As seen in FIG. 21(*a,b,c*), SEM analysis show that mycorrhizal fungi are present on the surface as well as within the pores of SNS-PHP near the surface. This is because of the filamentous nature of the fungi. FIG. 21(*a*) show the surface structure of the support PolyHIPE Polymer at low magnifications while FIGS. 21(*b*,c) are the high magnifications of sulphonated, neutralized spongy PolyHIPE Polymer and mycorrhizal fungi. The SSS-polymers which are already inoculated by mycorrhizal fungi can be further inoculated by *Rhizobium* as described previously. Alternatively, two different types of SNS-PHP inoculated with mycorrhizal fungi and *Rhizobium* can be mixed and used as co-soil additives. It is known that mycorrhizal fungi form a network between the roots of different species, such as nitrogen fixing plants (crops and trees) and non-legumes and transferring nitrogen between them. As the roots of these two types of plants are associated with the soil additive porous hydrophilic bioactive polymer containing either mycorrhizal fungi or rhizobia then nutrient transfer network is established through microbial root association.

SSS-Media as a Direct Root Delivery System

Figure 22:
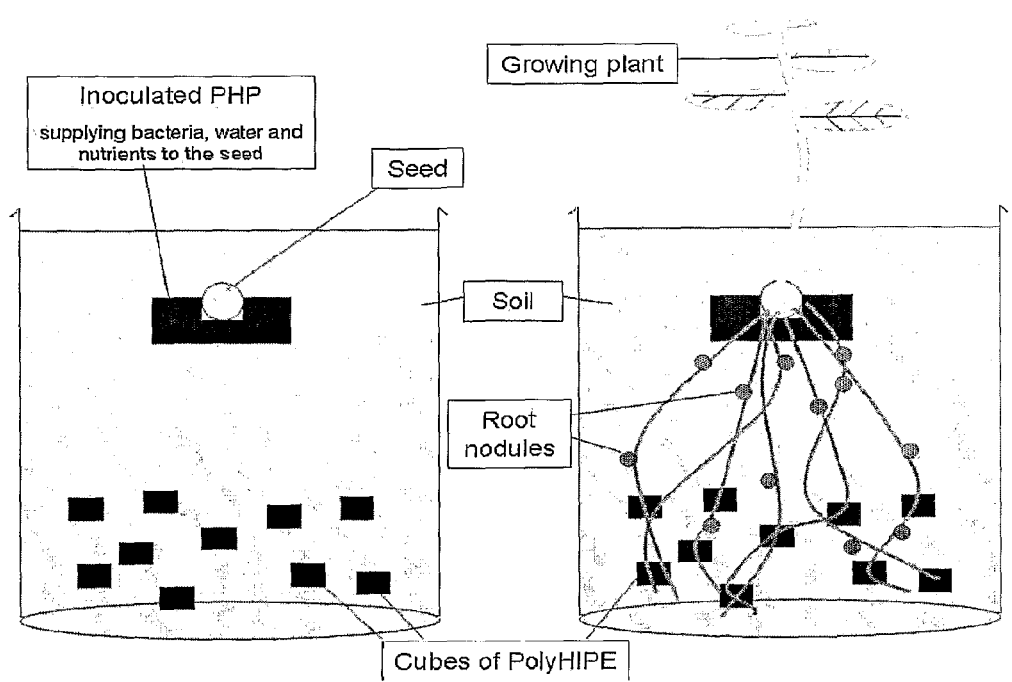
FIG. 22. Illustration of root growth and nodulation when plants are grown from seeds and subsequently transplanted. This technique is devised for the enhancement of plant survival in hostile environment.

The important feature of the SSS-media is that the delivery of water, nutrients, bacteria (through infection) are directly achieved through the plant roots because of the association of SSS-media with the roots. This is in contrast with the other delivery mechanisms where the soil is the main delivery vector. Therefore, the current technique is more efficient and environmentally friendly especially when other toxic agro-chemicals (such as pesticides, herbicides or indeed bacteria) are delivered. SSS-media can also be used to deliver seeds or seedlings as a package containing water, nutrients and bacteria in order enhance the survival of the plants until they are established in the soil. FIG. 22 illustrates diagrammatically such a seed/seedling package containing various types of SSS-media loaded with water, nutrients or bacteria and mixed together to provide a vehicle for the establishment of seed/seedling in their new environment. This system can also be used in the large scale plantation of trees in arid areas by dropping pots containing seeds or germinated seeds from airplanes (aerial plantation).

What is claimed is:

1. A plant growth support medium, the medium comprising a sulphonated polymeric material, having a primary pores of size greater than 30 micron, the polymeric material being elastic to enable the pores to increase in size.

2. A medium according to claim 1, wherein the primary pore size of the polymeric material is from 30-300 micron.

3. A medium according to claim 1, wherein the primary pore size of the polymeric material is from 50-150 micron.

4. A medium according to claim 3, wherein the degree of sulphonation is from 60-70%.

5. A medium according to claim 1, wherein the degree of sulphonation is from 40-75%.

6. A medium according to claim 1, wherein the pore wall is composed of fused granular-polymer.

7. A medium according to claim 6, wherein the grain size is of from 10-20 nanometres.

8. A medium according to claim 7, wherein the pore wall comprises pores of size 1-5nm.

9. A medium according to claim 1, wherein the polymeric material is a member selected from the group consisting of polystyrene, styrene/ethylhexyl acrylate copolymer and a styrene/vinylpyridine copolymer.

10. A medium according to claim 9, wherein the styrene/ethylhexyl acrylate copolymer has the components in a 75:20 weight ratio.

11. A medium according to claim 9, wherein copolymer has the components present in a 75:8 weight ratio.

12. A medium according to claim 1, wherein the polymeric material includes capillaries which are millimeter in size.

13. A medium according to claim 1, wherein the primary pores are interconnected.

14. A method of assisting plant growth, comprising the steps of:

providing an effective amount of a plant growth support medium, the medium comprising a sulphonated polymeric material, having a primary pores of size greater than 30 micron, the polymeric material being elastic to enable the pores to increase in size; and applying said effective amount of said plant growth support medium to a plant, thereby assisting plant growth through the retention of water, nutrients, and bioactive systems.

15. The method according to claim 14, wherein:

said step of applying said effective amount of said plant growth support medium is through association with the roots of the plants, thereby delivering active ingredients such as water, nutrients, bacteria or agrochemicals to the plant through the roots.

16. The method according to claim 14, comprising the additional step of:

providing a suitable environment to enhance root, water, nutrient, bacteria, fungi and root exudates interactions and communications.

* * * * *